United States Patent
Bi et al.

(10) Patent No.: US 9,862,724 B2
(45) Date of Patent: Jan. 9, 2018

(54) PYRAZOLO[1,5-A]PYRIMIDINE-BASED COMPOUNDS, COMPOSITIONS COMPRISING THEM, AND METHODS OF THEIR USE

(71) Applicant: LEXICON PHARMACEUTICALS, INC., The Woodlands, TX (US)

(72) Inventors: Yingzhi Bi, Plainsboro, NJ (US); Michael Walter Gardyan, Feasterville, PA (US); Michael Alan Green, Easton, PA (US); Godwin Kumi, Rocky Hill, CT (US); Yulian Zhang, Acton, MA (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 15/145,435

(22) Filed: May 3, 2016

(65) Prior Publication Data
US 2017/0081330 A1   Mar. 23, 2017

Related U.S. Application Data

(63) Continuation of application No. 14/478,089, filed on Sep. 5, 2014, now abandoned.

(60) Provisional application No. 61/874,395, filed on Sep. 6, 2013.

(51) Int. Cl.
| | |
|---|---|
| *C07D 487/04* | (2006.01) |
| *A61K 31/519* | (2006.01) |
| *A61P 25/02* | (2006.01) |
| *A61P 25/28* | (2006.01) |
| *A61P 25/16* | (2006.01) |
| *A61P 25/18* | (2006.01) |

(52) U.S. Cl.
CPC .......... *C07D 487/04* (2013.01); *A61K 31/519* (2013.01)

(58) Field of Classification Search
CPC ............................ C07D 487/04; A61K 31/519
See application file for complete search history.

(56) References Cited

U.S. PATENT DOCUMENTS

| | | |
|---|---|---|
| 2005/0130992 A1 | 6/2005 | Wichmann et al. |
| 2006/0217387 A1 | 9/2006 | McArthur et al. |
| 2007/0072879 A1 | 3/2007 | McArthur et al. |
| 2009/0275586 A1 | 11/2009 | Govek et al. |
| 2010/0311729 A1 | 12/2010 | Capraro et al. |
| 2010/0331314 A1 | 12/2010 | Mustapha et al. |
| 2013/0253194 A1 | 9/2013 | Bi et al. |
| 2014/0080834 A1 | 3/2014 | Lanthorn et al. |

FOREIGN PATENT DOCUMENTS

| | | |
|---|---|---|
| WO | WO2011073316 | 6/2011 |
| WO | WO2012156756 | 11/2012 |
| WO | WO2013147711 | 10/2013 |

OTHER PUBLICATIONS

International Search Report for International Application No. PCT/US2014/054209 filed Sep. 5, 2014.
Gupta, U. et al., "Synthesis of Some New Pyrazolo . . . ", *Heterocyclic Letters*, 2012, 2(1): 150-153.
Large, J.M., et al., "Imidazopyridazines and Potent Inhibitors . . . ", *Bioog. Med. Chem. Let.*, 2013, 23(21): 6019-6024.

*Primary Examiner* — Susanna Moore
(74) *Attorney, Agent, or Firm* — Max Bachrach

(57) ABSTRACT

Pyrazolo[1,5-a]pyrimidine-based compounds of the formula:

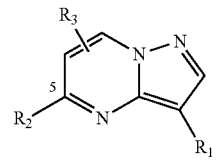

are disclosed, wherein $R_1$, $R_2$ and $R_3$ are defined herein. Compositions comprising the compounds and methods of their use to treat, manage and/or prevent diseases and disorders mediated by mediated by adaptor associated kinase 1 activity are also disclosed.

13 Claims, 1 Drawing Sheet

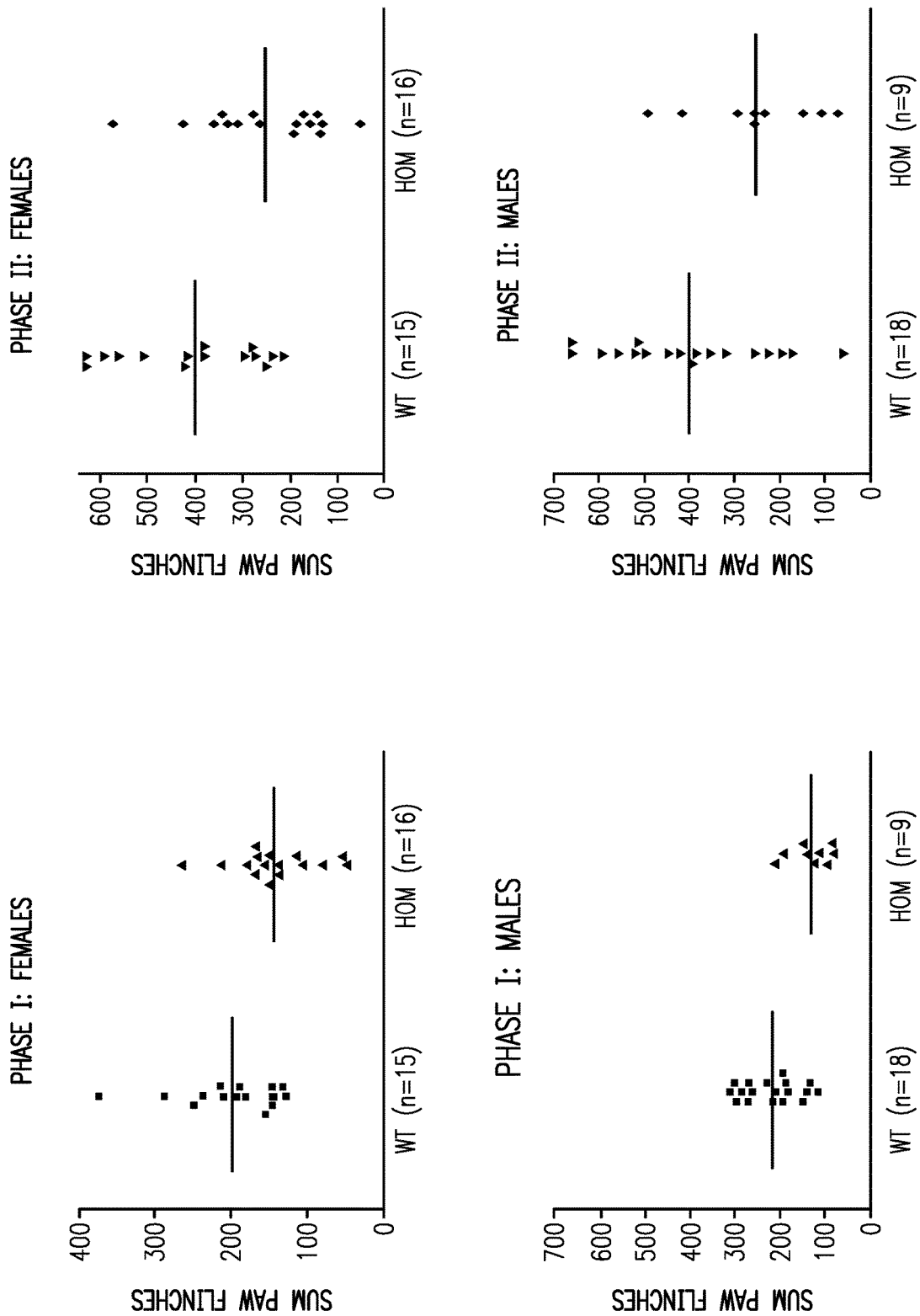

PYRAZOLO[1,5-A]PYRIMIDINE-BASED COMPOUNDS, COMPOSITIONS COMPRISING THEM, AND METHODS OF THEIR USE

This application is a continuation of U.S. patent application Ser. No. 14/478,089, filed Sep. 5, 2014, which claims priority to U.S. provisional patent application No. 61/874,395, filed Sep. 6, 2013, the entireties of which are incorporated herein by reference.

1. FIELD OF THE INVENTION

This invention is directed to pyrazolo[1,5-a]pyrimidine-based compounds useful as inhibitors of adaptor associated kinase 1 (AAK1), compositions comprising them, and methods of their use.

2. BACKGROUND OF THE INVENTION

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., *Proc. Natl. Acad. Sci. USA.* 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, bipolar disorder, and Alzheimer's disease.

3. SUMMARY OF THE INVENTION

This invention is directed, in part, to AAK1 inhibitors of the formula:

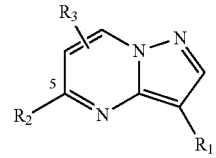

and pharmaceutically acceptable salts thereof, wherein: $R_1$ is $R_{1A}$ or optionally substituted $C_{1-12}$ hydrocarbyl or 2-12-membered heterocarbyl, which optional substitution is with one or more $R_{1A}$; each $R_{1A}$ is independently $-OR_{1C}$, $-N(R_{1C})_2$, $-C(O)R_{1C}$, $-C(O)OR_{1C}$, $-C(O)N(R_{1C})_2$, $-N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently $-OR_{1C}$, $-N(R_{1C})_2$, $-C(O)R_{1C}$, $-C(O)OR_{1C}$, $-C(O)N(R_{1C})_2$, $-N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; $R_2$ is optionally substituted $C_{1-12}$ hydrocarbyl or 2-12-membered heterocarbyl bound to C5 by one of its carbon atoms, which optional substitution is with one or more $R_{2C}$; each $R_{2C}$ is independently $-OR_{2D}$, $-N(R_{2D})_2$, $-C(O)R_{2D}$, $-C(O)OR_{2D}$, $-C(O)N(R_{2D})_2$, $-N(R_{2D})C(O)OR_{2D}$, cyano, halo, oxo, or optionally substituted $C_{1-12}$ hydrocarbyl or 2-12-membered heterocarbyl, which optional substitution is with one or more amino, cyano, halo, hydroxyl, or $R_{2D}$; each $R_{2D}$ is independently hydrogen or optionally substituted $C_{1-12}$ hydrocarbyl or 2-12-membered heterocarbyl, which optional substitution is with one or more amino, cyano, halo, or hydroxyl; and $R_3$ is hydrogen or $C_{1-6}$ alkyl optionally substituted with one or more cyano, halo or hydroxyl.

One embodiment of the invention encompasses pharmaceutical compositions and dosage forms comprising a compound disclosed herein (i.e., a compound of the invention).

Another embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Examples of such diseases and disorders are believed to include Alzheimer's disease, bipolar disorder, pain, Parkinson's disease, and schizophrenia (including cognitive deficits in schizophrenia).

4. BRIEF DESCRIPTION OF THE FIGURES

Aspects of the invention are illustrated in FIG. 1, which shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

5. DETAILED DESCRIPTION OF THE INVENTION

This invention is based, in part, on the discovery that AAK1 knockout mice exhibit a high resistance to pain. That discovery prompted research that ultimately led to the discovery of AAK1 inhibitors, compositions comprising them, and methods of their use.

5.1. DEFINITIONS

Unless otherwise indicated, the phrases "compounds of the invention," "compounds of the present disclosure," and the like refer to the compounds disclosed herein.

Unless otherwise indicated, the term "hydrocarbyl" means an aliphatic or alicyclic moiety having an all-carbon backbone and consisting of carbon and hydrogen atoms. Examples of hydrocarbyl groups include those having 1-20, 1-12, 1-6, and 1-4 carbon atoms (referred to as $C_{1-20}$ hydrocarbyl, $C_{1-12}$ hydrocarbyl, $C_{1-6}$ hydrocarbyl, and $C_{1-4}$ hydrocarbyl, respectively). Particular examples include alkyl, alkenyl, alkynyl, aryl, benzyl, cycloalkyl, cycloalkenyl, cycloalkylalkyl, cycloalkenylalkyl, napthyl, phenyl, and phenylethyl.

Examples of alkyl moeites include straight-chain and branched moieties having 1-20, 1-12, 1-6, 1-4 and 1-3 carbon atoms (referred to as $C_{1-20}$ alkyl, $C_{1-12}$ alkyl, $C_{1-6}$ alkyl, $C_{1-4}$ alkyl and $C_{1-3}$ alkyl, respectively). Particular examples include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl.

Examples of alkenyl moieties include straight-chain and branched $C_{2-20}$, $C_{2-12}$ and $C_{2-6}$ alkenyl. Particular examples include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Examples of alkynyl moeites include include straight-chain and branched $C_{2-20}$, $C_{2-12}$ and $C_{2-6}$ alkynyl. Particular examples include ethynyl and 2-propynyl(propargyl).

Examples of aryl moeites include anthracenyl, azulenyl, fluorenyl, indan, indenyl, naphthyl, phenyl and phenanthrenyl.

Examples of cycloalkyl moeites include $C_{3-12}$, $C_{3-7}$, $C_{4-6}$ and $C_6$ cycloalkyl. Particular examples include cyclopropyl, cyclobutyl, cyclopentyl, cyclohexyl and adamantyl.

Unless otherwise indicated, the term "halo" encompass fluoro, chloro, bromo, and iodo.

Unless otherwise indicated, the term "heterocarbyl" refers to a moiety having a backbone made up of one or more carbon atoms and one or more heteroatoms. Particular heteroatoms are nitrogen, oxygen and sulfur. A heterocarbyl moieties can be thought of as a hydrocarbyl moiety wherein at least one carbon atom, $CH$, $CH_2$, or $CH_3$ group is replaced with one or more heteroatoms and the requisite number of hydrogen atoms to satisfy valencies. Examples of heterocarbyl include 2-20, 2-12, 2-8, 2-6 and 2-4 membered heterocarbyl moieties, wherein the number range refers to the sum total of carbon, nitrogen, oxygen, and/or sulfur atoms in the moiety. The term "2-12 membered heterocarbyl" thus refers to a heterocarbyl moiety having a total of 2-12 carbon, nitrogen, oxygen, and/or sulfur atoms. Particular heterocarbyl moeites include straight chain and branched heteroalkyl, heteroalkenyl, and heteroalkynyl, as well as heterocycle and heteroaryl.

Examples of heteroalkyl moieties include 2-8-membered, 2-6-membered and 2-4-membered heteroalkyl moieties. Particular examples include alkoxyl, acyl (e.g., formyl, acetyl, benzoyl), alkylamino (e.g., di-($C_{1-3}$-alkyl)amino), arylamino, aryloxime, carbamates, carbamides, alkylcarbonyl, arylcarbonyl, aminocarbonyl, alkylaminocarbonyl, alkylsulfanyl, arylsulfanyl, alkylsulfinyl, arylsulfinyl, alkylsulfonyl, arylsulfonyl, alkylsulfonylamino, and arylsulfonylamino.

Unless otherwise indicated, the term "heterocycle" refers to a cyclic (monocyclic or polycyclic) heterocarbyl moieity which may be aromatic, partially aromatic or non-aromatic. Heterocycles include heteroaryls. Examples include 4-10-membered, 4-7-membered, 6-membered, and 5-membered heterocycles. Particular examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl. Because the term "heterocycle" refers to a ring, standing alone it does not encompass moieities such as oxazolidinone and imidazolidinone: such moieties are considered substituted heterocycles, viz. heterocycles substituted with oxo.

Examples of heteroaryl moieties include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

5.2. COMPOUNDS

This invention encompasses compounds of the formula:

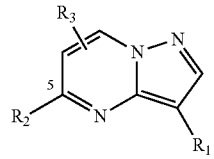

and pharmaceutically acceptable salts thereof, wherein: $R_1$ is $R_{1A}$ or optionally substituted $C_{1-12}$ hydrocarbyl or 2-12-membered heterocarbyl, which optional substitution is with one or more $R_{1A}$; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; $R_2$ is optionally substituted $C_{1-12}$ hydrocarbyl or 2-12-membered heterocarbyl bound to C5 by one of its carbon atoms, which optional substitution is with one or more $R_{2C}$; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, oxo, or optionally substituted $C_{1-12}$ hydrocarbyl or 2-12-membered heterocarbyl, which optional substitution is with one or more amino, cyano, halo, hydroxyl, or $R_{2D}$; each $R_{2D}$ is independently hydrogen or optionally substituted $C_{1-12}$ hydrocarbyl or 2-12-membered heterocarbyl, which optional substitution is with one or more amino, cyano, halo, or hydroxyl; and $R_3$ is hydrogen or $C_{1-6}$ alkyl optionally substituted with one or more cyano, halo or hydroxyl. The term "C5" refers to the carbon atom labeled with a "5" on the core structure depicted above.

Some compounds of the invention are of the formula:

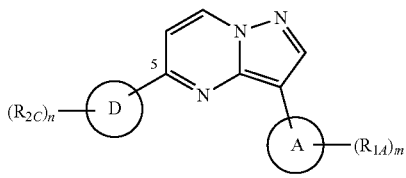

wherein: A is cyclic C1-12 hydrocarbyl or 4-7-membered heterocycle; D is cyclic C1-12 hydrocarbyl or 4-7-membered heterocycle bound to C5 by one of its carbon atoms; n is 1-3; and m is 0-3.

Some are of the formula:

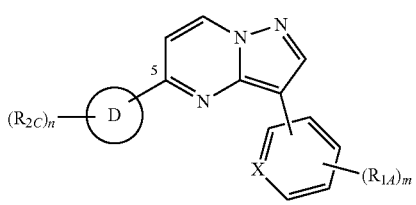

wherein X is CH or N.

Some are of the formula:

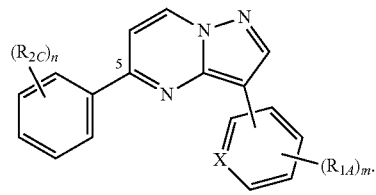

Some are of the formula:

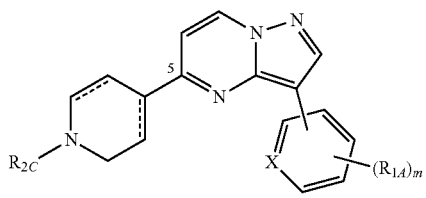

wherein $R_{2C}$ is —$C(O)R_{2D}$, —$C(O)OR_{2D}$, or optionally substituted C1-12 hydrocarbyl or 2-12-membered heterocarbyl, which optional substitution is with one or more amino, cyano, halo, hydroxyl, or $R_{2D}$.

Some are of the formula:

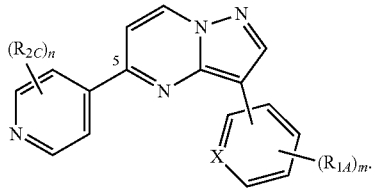

Some are of the formula:

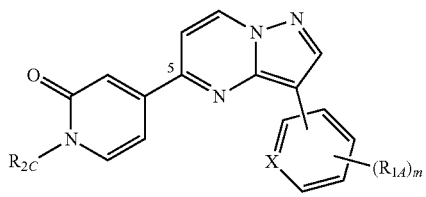

wherein $R_{2C}$ is —$C(O)R_{2D}$, —$C(O)OR_{2D}$, or optionally substituted $C_{1-12}$ hydrocarbyl or 2-12-membered heterocarbyl, which optional substitution is with one or more amino, cyano, halo, hydroxyl, or $R_{2D}$.

Some are of the formula:

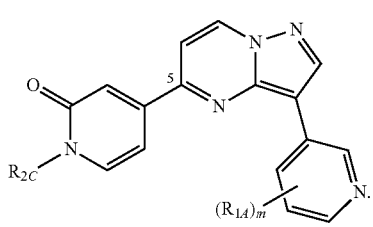

Some are of the formula:

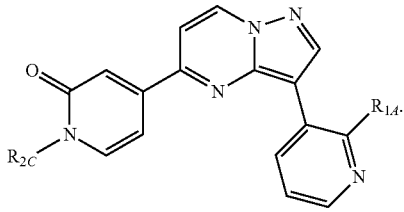

Some are of the formula:

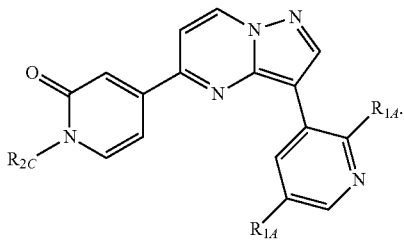

Referring the various formulae disclosed herein, embodiments of the invention encompass compounds wherein one or more of the following are satisfied:

D is piperazin or pyrrolidin
n is 2
m is 1
A is pyridinyl, thiophen, or imidazol
$R_1$ is $R_{1A}$
$R_1$ is optionally substituted $C_{1-12}$ hydrocarbyl
$R_1$ is optionally substituted phenyl
$R_1$ is optionally substituted 2-12-membered heterocarbyl (e.g., 2-8 membered heterocarbyl, 2-6 membered heterocarbyl, 2-6 membered heterocarbyl)
$R_1$ is optionally substituted pyridinyl, thiophen, or imidazol
$R_{1A}$ is halo
$R_{1A}$ is $-OR_{1C}$, $-N(R_{1C})_2$, $-C(O)R_{1C}$, $-C(O)OR_{1C}$, or $-C(O)N(R_{1C})_2$
$R_{1A}$ is $-OR_{1C}$
$R_{1B}$ is $-N(R_{1C})_2$, $-OR_{1C}$, halo
$R_{1C}$ is hydrogen
$R_{1C}$ is $C_{1-12}$ hydrocarbyl (e.g., $C_{1-6}$ hydrocarbyl, $C_{1-4}$ hydrocarbyl such as methyl, ethyl, propyl)
$R_2$ is 6-membered heterocycle
$R_2$ is $C_{1-6}$ hydrocarbyl
$R_{2C}$ is $C_{1-12}$ hydrocarbyl
$R_{2D}$ is halo
$R_{2D}$ is optionally substituted $C_{1-12}$ hydrocarbyl, which optional substitution is with one or more of amino, cyano, halo, hydroxyl
$R_{2D}$ is 2-12-membered heterocarbyl comprising at least one nitrogen atom
$R_3$ is hydrogen In structures shown herein, bonds depicted by a solid line and a dashed line are either single double bonds. Thus, the moiety

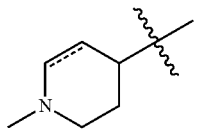

encompasses both of the following:

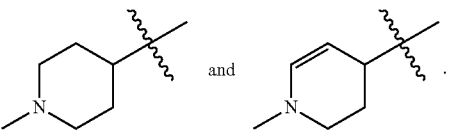

Compounds of the invention can have one or more asymmetric centers. Unless otherwise indicated, this invention encompasses all stereoisomers of the compounds, as well as mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

Particular compounds of the invention inhibit AAK1 with an $IC_{50}$ of less than 0.1, 0.01 or 0.001 µM as measured in the P81 filter plate assay described below in the Examples. Particular compounds of the invention inhibit AAK1 with an $IC_{50}$ of less than 0.1, 0.01 or 0.001 µM as measured in the HEK281 cell-based assay described described below in the Examples.

5.3. METHODS OF SYNTHESIS

Compounds of the present invention (i.e., compounds disclosed herein) can be prepared using the methods described below and using methods known to those skilled in the art of organic chemistry. Particular compounds are of the general formula:

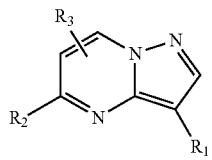

wherein $R_1$, $R_2$ and $R_3$ are defined herein, and include salts thereof. These compounds can prepared by the methods outlined below.

Compounds of formula shown above can be prepared by the methods outlined below. Scheme 1 shows an approach useful in preparing compounds of the invention wherein $R_2$ is aryl (including heteroaryl and pyridone analogs). Here, the Suzuki coupling of compound 1 with an appropriate boronic acid or ester [$R_3B(OR)_2$] provides 2. Bromination of 2 affords intermediate 3. Second Suzuki coupling gives compound 4.

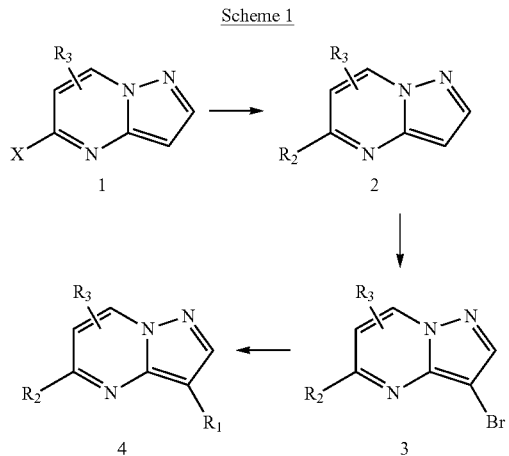

Scheme 2 shows an approach useful in preparing compounds of the invention wherein $R_2$ is hydrocarbyl and R' is $R_{2C}$, $R_{2D}$, or a precursor thereof. Here, the Suzuki, Heck or other coupling of compound 10 with an appropriate boronic acid, ester [$R_3B(OR)_2$] or alkene provides 11. Reduction of the alkene in 11 gives compound 12. Bromination of 12 affords intermediate 13. Second Suzuki coupling gives compound 14.

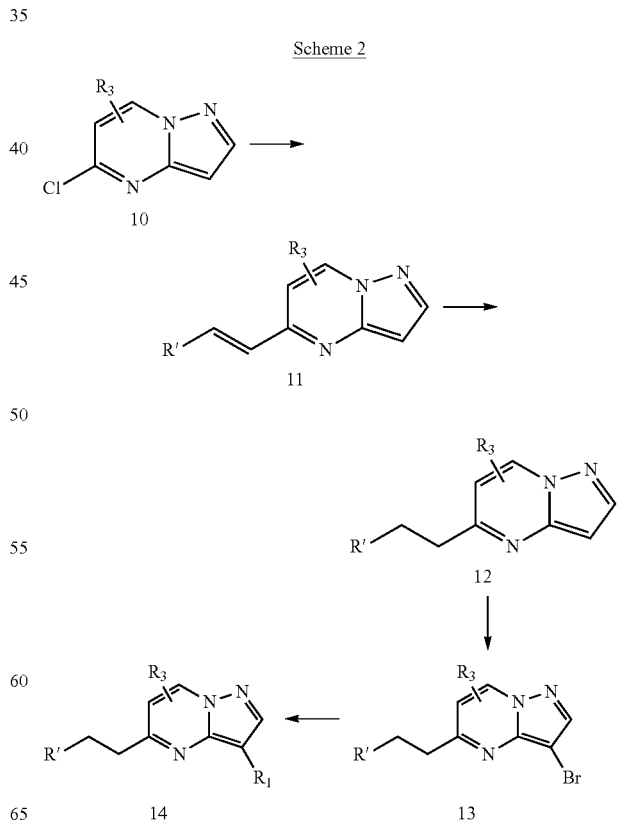

5.4. METHODS OF USE

One embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Diseases and disorders mediated by AAK1 activity are diseases and disorders that have at least one symptom, the severity or manifestation of which is affected by AAK1 activity. Examples of such diseases and disorders are believed to include Alzheimer's disease, bipolar disorder, pain, Parkinson's disease, and schizophrenia (including cognitive deficits in schizophrenia). Particular methods comprise administering to a patient (a human or other mammal) in need thereof a therapeutically or prophylactically effective amount of an AAK1 inhibitor (e.g., a compound disclosed herein).

Another embodiment of this invention encompasses a method of treating or managing a disease or disorder, which comprises administering to a patient in need thereof a therapeutically or prophylactically effective amount of an AAK1 inhibitor, wherein the disease or disorder is Alzheimer's disease, bipolar disorder, pain, Parkinson's disease, or schizophrenia (including cognitive deficits in schizophrenia). Particular types of pain include chronic pain, acute pain, and neuropathic pain. Particular types of neuropathic pain include fibromyalgia and peripheral neuropathy (e.g., diabetic neuropathy).

When used to treat or manage a disease or disorder, compounds of the invention are preferably administered as part of a pharmaceutical composition comprising one or more pharmaceutically acceptable carriers, diluents or excipients.

Pharmaceutical compositions, or formulations, may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

Compounds of the invention may be administered in combination with one or more additional therapeutic or prophylactic agents. For example, when used for the treatment of pain, possible additional agents include immunosuppressive and anti-inflammatory agents.

Immunosuppressants suitable for use in the methods and compositions of this invention include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Additional examples include inosine monophosphate dehydrogenase inhibitors, such as mycophenolate mofetil (CellCept®) and mycophenolic acid (Myfortic®).

Anti-inflammatory drugs suitable for use in the methods and compositions of this invention include those known in the art. Examples include glucocorticoids and NSAIDs.

Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the invention may be administered in combination with one or more additional therapeutic or prophylactic agents directed at the underlying disease or condition. For example, when used to treat diabetic neuropathy, compounds of the invention may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

5.5. PHARMACEUTICAL COMPOSITIONS

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

5.6. EXAMPLES

Certain aspects of the invention can be understood from the following examples.

5.6.1. AAK1 Knockout Mice

Mice homozygous (−/−) for the disruption of the AAK1 gene were prepared by two methods: gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 μl of 5% formalin is subcutaneously injected in the dorsal surface of the left hind paw. Mice were individually housed in cylindrical chambers for 45 minutes. A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. *An automated flinch detecting system for use in the formalin nociceptive bioassay.* J Appl Physiol., 2001; 90:2386-402.

As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

5.6.2. Synthesis of Tert-butyl 4-(pyrazolo[1,5-a]pyrimidin-5-yl)-5,6-dihydropyridine-1(2H)-carboxylate

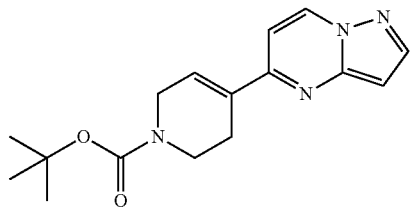 [SMILES: CC(C)(C)OC(=O)N1CC=C(c2ccn3nccc3n2)CC1]

5-Chloropyrazolo[1,5-a]pyrimidine (307 mg, 2 mmol) taken up in 4 ml DME and 2 ml water. Tert-butyl 4-(4,4,5,5-tetra methyl-1,3,2-dioxaborolan-2-yl)-5,6-dihydropyridine-1(2H)-carboxylate (650 mg, 2.2 mmol), sodium carbonate (421 mg, 4 mmol), and Pd(dppf)Cl$_2$:DCM (164 mg, 0.2 mmol) added and reaction stirred in microwave in a sealed tube at 150° C. for 15 minutes. The reaction mixture was cooled and filtered through celite, washed with ethyl acetate, and concentrated. Pure product was obtained from Prep HPLC. $^1$H NMR (400 MHz, METHANOL-d$_4$) δ ppm 1.52 (s, 9H) 2.71-2.76 (m, 2H) 3.66 (t, J=5.68 Hz, 2H) 4.20 (br. s., 2H) 6.63 (d, J=2.27 Hz, 1H) 6.82 (br. s., 1H) 7.28 (d, J=7.58 Hz, 1H) 8.10 (d, J=2.27 Hz, 1H) 8.75 (d, J=7.58 Hz, 1H). LRMS (ESI) m/z 301.0 [(M+H)]$^+$, calc'd for C$_{16}$H$_{20}$N$_4$O$_2$: 300.4.

5.6.3. Synthesis of Isopropyl 4-(3-(2-methoxypyridin-3-yl)pyrazolo[1,5-a]pyrimidin-5-yl)-5,6-dihydropyridine-1(2H)-carboxylate

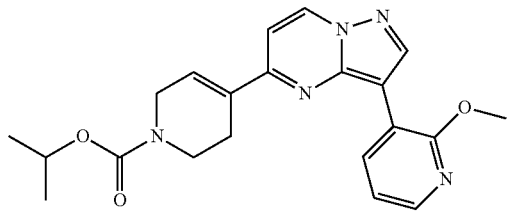 [SMILES: COc1ncccc1-c1cnn2ccc(C3=CCN(C(=O)OC(C)C)CC3)nc12]

Part A. 5-(1,2,3,6-Tetrahydropyridin-4-yl)pyrazolo[1,5-a]pyrimidine

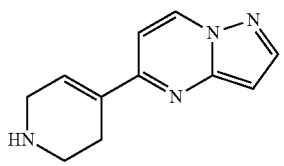 [SMILES: C1=C(c2ccn3nccc3n2)CCNC1]

To a solution of tert-butyl 4-(pyrazolo[1,5-a]pyrimidin-5-yl)-5,6-dihydropyridine-1(2H)-carboxylate (2.4 g, 8 mmol) in MeOH (30 ml) was added acetyl chloride (5.7 ml). The resulting mixture was stirred overnight at room temperature. The mixture was concentrated to give the titled compound (1.9 g). The analytical sample was obtained from prep HPLC as a formic salt. $^1$H NMR (400 MHz, METHANOL-d$_4$) δ ppm 3.00 (ddt, J=6.06, 4.04, 2.02, 2.02 Hz, 2H) 3.48 (t, J=6.19 Hz, 2H) 3.95-3.98 (m, 2H) 6.68 (d, J=2.27 Hz, 1H) 6.88 (dt, J=3.54, 1.77 Hz, 1H) 7.34 (d, J=7.58 Hz, 1 H) 8.15 (d, J=2.27 Hz, 1H) 8.53 (br. s., 0.5H) 8.84 (d, J=7.58 Hz, 1H). LRMS (ESI) m/z 201.0 [(M+H)]$^+$, calc'd for C$_{11}$H$_{12}$N$_4$: 200.25.

Part B. Isopropyl 4-(pyrazolo[1,5-a]pyrimidin-5-yl)-5,6-dihydropyridine-1(2H)-carboxylate

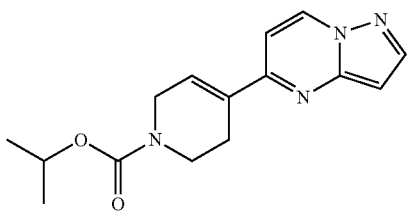 [SMILES: CC(C)OC(=O)N1CC=C(c2ccn3nccc3n2)CC1]

A mixture of 5-(1,2,3,6-tetrahydropyridin-4-yl)pyrazolo[1,5-a]pyrimidine (1.9 g, 8 mmol), isopropyl chloroformate (1 M in toluene, 9.6 ml, 9.6 mmol) and TEA (3.2 ml, 24 mmol) in DCM (50 ml) was stirred at room temperature for overnight. The mixture was washed with water, dried and concentrated. The residue was subjected to ISCO to give the isopropyl carbamate (1.3 g).

Part C. Isopropyl 4-(3-(2-methoxypyridin-3-yl)pyrazolo[1,5-a]pyrimidin-5-yl)-5,6-dihydropyridine-1(2H)-carboxylate

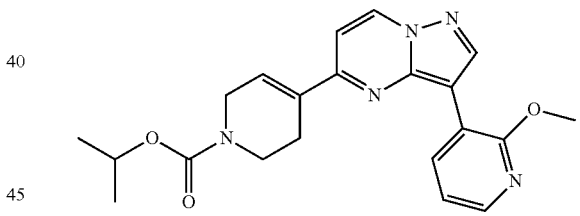

A mixture of isopropyl 4-(pyrazolo[1,5-a]pyrimidin-5-yl)-5,6-dihydropyridine-1(2H)-carboxylate (1.2 g, 4.2 mmol) and Br$_2$ (0.32 ml, 6.3 mmol) in AcOH (20 ml) was stirred at room temperature for 2 h. The mixture was concentrated to give 2.5 g brown oil.

A mixture of above brown oil, (2-methoxypyridin-3-yl)boronic acid (851 mg, 5 mmol), sodium carbonate (1.33 g, 12.6 mmol), and Pd(dppf)Cl$_2$:DCM (343 mg, 0.42 mmol) in DME (20 ml) and water (10 ml) was stirred at 90° C. overnight. Reaction was cooled, filtered and concentrated. The residue was subjected to ISCO then Prep HPLC to afford the titled compound. $^1$H NMR (400 MHz, METHANOL-d$_4$) δ ppm 1.32 (d, J=6.32 Hz, 6H) 2.81 (br. s., 2H) 3.73 (t, J=5.56 Hz, 2H) 4.10 (s, 3H) 4.26 (br. s., 2H) 4.96 (m, 1H) 6.90 (br. s., 1H) 7.08 (dd, J=7.58, 5.05 Hz, 1H) 7.34 (d, J=7.58 Hz, H) 8.04 (dd, J=5.05, 1.77 Hz, 1H) 8.71 (s, 1H) 8.76 (d, J=7.58 Hz, 1H) 8.95 (dd, J=7.58, 1.77 Hz, 1H). LRMS (ESI) m/z 394.1 [(M+H)]$^+$, calc'd for C$_{21}$H$_{23}$N$_5$O$_3$: 393.45.

5.6.4. Synthesis of Isopropyl 4-(3-(2-methoxypyridin-3-yl)pyrazolo[1,5-a]pyrimidin-5-yl)piperidine-1-carboxylate

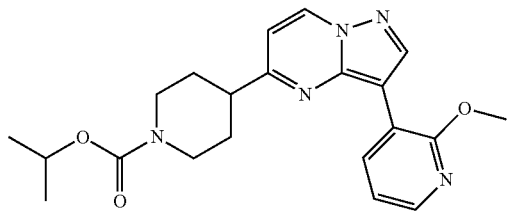 [SMILES: COc1ncccc1-c1cnn2ccc(C3CCN(C(=O)OC(C)C)CC3)nc12]

Isopropyl 4-(3-(2-methoxypyridin-3-yl)pyrazolo[1,5-a]pyrimidin-5-yl)-5,6-dihydropyridine-1(2H)-carboxylate was subjected to hydrogenation with 5% Pd/C in MeOH to afford the titled compound. $^1$H NMR (400 MHz, METHANOL-d$_4$) δ ppm 1.30 (d, J=6.32 Hz, 6H) 1.76-1.87 (m, 2H) 2.05-2.08 (m, 2H) 2.97-3.14 (m, 3H) 4.09 (s, 3H) 4.27-4.31 (m, 2H) 4.92 (m, 1H) 7.04 (d, J=7.07 Hz, 1H) 7.08 (dd, J=7.58, 1.77 Hz, 1H) 8.04 (dd, J=4.93, 1.89 Hz, 1H) 8.74 (s, 1H) 8.82 (d, J=7.07 Hz, 1H) 8.96 (dd, J=7.58, 1.77 Hz, 1H). LRMS (ESI) m/z 396.1 [(M+H)]$^+$, calc'd for C$_{21}$H$_{25}$N$_5$O$_3$: 395.46.

5.6.5. Synthesis of (5-(2-Isopropoxypyridin-4-yl)pyrazolo[1,5-a]pyrimidin-3-yl)methanol

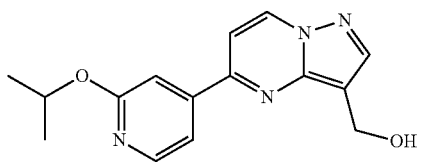 [SMILES: CC(C)Oc1cc(-c2ccn3ncc(CO)c3n2)ccn1]

(5-Chloropyrazolo[1,5-a]pyrimidin-3-yl)methanol (600 mg, 3.9 mmol) taken up in 3 ml acetonitrile and 1.5 ml water. 2-isopropoxy-4-(4,4,5,5-tetramethyl-1,3,2-dioxaborolan-2-yl)pyridine (1 g, 3.9 mmol), potassium carbonate (1.07 g, 7.8 mmol), and Pd(dppf)Cl$_2$:DCM (319 mg, 0.39 mmol) added and reaction stirred in microwave in a sealed tube at 120° C. for 12 minutes. Reaction was cooled, filtered through celite and reduced in vacuo. Reaction purified on Shimadzu neutral phase prep, lyopholized to obtain 96 mg product. $^1$H NMR (DMSO-d$_6$) δ: 9.21 (d, J=7.3 Hz, 1H), 8.33 (d, J=5.6 Hz, 1H), 8.27 (s, 1H), 7.74 (dd, J=5.4, 1.4 Hz, 1H), 7.71 (d, J=7.3 Hz, 1H), 7.54 (d, J=0.8 Hz, 1H), 5.28-5.40 (m, 1H), 5.03 (s, 1H), 4.75 (d, J=5.3 Hz, 2H), 1.34 (d, J=6.1 Hz, 6H) LRMS (ESI) m/z 285 [(M+H)]$^+$, calc'd for C$_{15}$H$_{16}$N$_4$O$_2$: 284.32.

5.6.6. Synthesis of Isopropyl(3-(3-(2-methoxypyridin-3-yl)pyrazolo[1,5-a]pyrimidin-5-yl)propyl)(methyl)carbamate

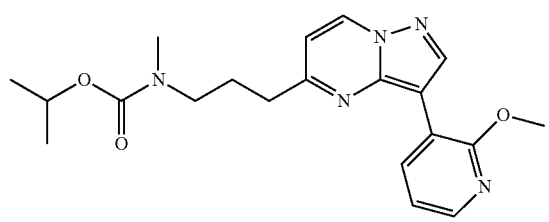 [SMILES: COc1ncccc1-c1cnn2ccc(CCCN(C)C(=O)OC(C)C)nc12]

Part A. Isopropyl allyl(methyl)carbamate

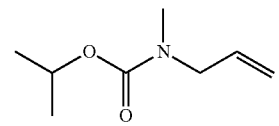

To 213 mg (3.00 mmol) of N-methylprop-2-en-1-amine in 20 mL EtOAc was added 3.6 mL (3.6 mmol) of isopropyl chloroformate (1M toluene solution), followed by 0.83 mL (6.00 mmol) of triethylamine. This mixture was stirred at room temperature for 1 hr. It was diluted with EtOAc, quenched with 5 mL water, washed with brine, dried over MgSO$_4$, concentrated on the rotavap, and carried forward for the next step without further purification. The yield was assumed to be theoretical.

Part B. Isopropyl methyl(3-(pyrazolo[1,5-a]pyrimidin-5-yl)propyl)carbamate

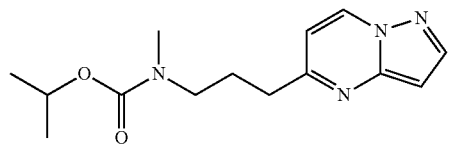 [SMILES: CC(C)OC(=O)N(C)CCCc1ccn2nccc2n1]

To the 3 mmol of isopropyl allyl(methyl)carbamate dissolved in 10 mL of THF at 0° C. was added 7.8 mL (3.9 mmol) 9-BBN (0.5 M THF solution), and the resulting mixture. The temperature was maintained at 0° C. for 0.25 hr, and then heated to 60° C. for 2.5 hr. To this was added 554 mg (3.6 mmol) of 5-chloropyrazolo[1,5-a]pyrimidine, 828 mg (6.00 mmol) of K$_2$CO$_3$, 346 mg (0.3 mmol) Pd(PPh$_3$)$_4$, 20 mL THF, 4 mL water, and 1 mL DMF. The resulting mixture was refluxed (65° C.) overnight. It was cooled to room temperature, diluted with EtOAc, washed with brine, dried over MgSO$_4$, concentrated on the rotavap, and purified on the ISCO to obtain 483 mg of the desired product (58% yield over two steps). $^1$H NMR (400 MHz, CHLOROFORM-d) δ ppm 1.23 (d, J=6.06 Hz, 6H) 2.05 (quin, J=7.26 Hz, 2H) 2.81-2.99 (m, 5H) 3.39 (br. s., 2H) 4.91 (dt, J=12.06, 5.97 Hz, 1H) 6.59 (d, J=1.77 Hz, 1H) 6.72 (br. s., 1H) 8.09 (d, J=2.27 Hz, 1H) 8.57 (d, J=7.33 Hz, 1H). LRMS (ESI) m/z 277 [(M+H)]$^+$, calc'd for C$_{14}$H$_{20}$N$_4$O$_2$: 276.

Part C. Isopropyl(3-(3-bromopyrazolo[1,5-a]pyrimidin-5-yl)propyl)(methyl)carbamate

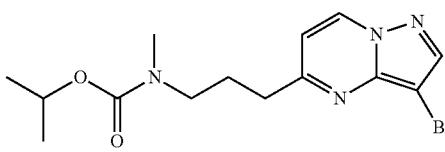

To 276 mg (1.00 mmol) of isopropyl methyl(3-(pyrazolo[1,5-a]pyrimidin-5-yl)propyl)carbamate dissolved in 10 mL of AcOH at room temperature was added 77 μL (1.50 mmol)

of bromine, and the resulting solvent stirred at room temperature. After 0.25 hr, LCMS indicates the reaction had gone to completion. It was concentrated to dryness on the rotavap, and then diluted with EtOAc. This was then washed with aqueous $Na_2CO_3$, dried over $MgSO_4$, and concentrated on the rotavap again. The crude mixture was purified on the ISCO, eluting with 20-100% EtOAc/hex to obtain 241 mg (68%) of the desired product. LRMS (ESI) m/z 355 [(M+H)]+, (doublet at 357), calc'd for $C_{14}H_{19}BrN_4O_2$: 354.

Part D. Isopropyl(3-(3-(2-methoxypyridin-3-yl)pyrazolo[1,5-a]pyrimidin-5-yl)propyl)(methyl)carbamate

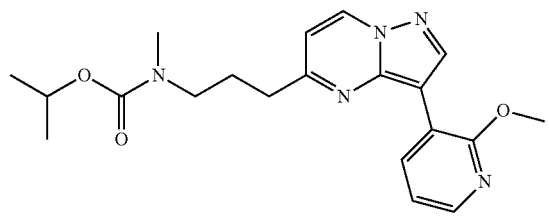 [SMILES: COc1ncccc1-c1cnn2ccc(CCCN(C)C(=O)OC(C)C)nc12]

To 100 mg (0.28 mmol) of isopropyl(3-(3-bromopyrazolo[1,5-a]pyrimidin-5-yl)propyl)(methyl) carbamate in a microwaveable vial was added 86 mg (0.563 mmol) of the (2-methoxypyridin-3-yl) boronic acid, followed by 178 mg (0.84 mmol) of $K_3PO_4$, 32 mg (0.03 mmol) of $Pd(PPh_3)_4$, 3 mL of MeCN, and 1.5 mL water. This was then microwaved for 0.5 hr at 140° C. It was diluted with EtOAc, washed with brine, dried over $MgSO_4$, concentrated and purified on the PREP HPLC to obtain the desired product. $^1$H NMR (400 MHz, CHLOROFORM-d) δ ppm 1.24 (br. s., 6H) 2.12 (quin, J=7.14 Hz, 2H) 2.92 (t, J=7.45 Hz, 5H) 3.43 (t, J=6.82 Hz, 2H) 4.12 (s, 3H) 4.86-5.00 (m, 1H) 6.76 (br. s., 1H) 7.04 (dd, J=7.45, 4.93 Hz, 1H) 8.10 (dd, J=4.93, 1.89 Hz, 1H) 8.60 (d, J=7.07 Hz, 1H) 8.79 (s, 1H) 8.88 (d, J=7.07 Hz, 1H). LRMS (ESI) m/z 384 [(M+H)]+, calc'd for $C_{20}H_{25}N_5O_3$: 383.

5.6.7. Synthesis of 4-(3-Bromopyrazolo[1,5-a]pyrimidin-5-yl)-1-isopentylpyridin-2(1H)-one

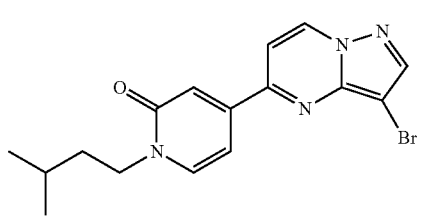 [SMILES: CC(C)CCn1ccc(-c2ccn3ncc(Br)c3n2)cc1=O]

Part A. 4-Bromo-1-isopentylpyridin-2(1H)-one

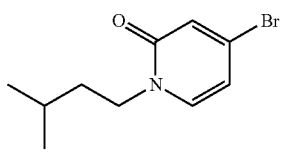

4-bromo-2-hydroxy pyridine (600 mg, 3.4 mmol) taken up in dry DMF under nitrogen. Sodium hydride 60% in oil (165 mg, 4.1 mmol) added and stirred 30 minutes. Lithium bromide (598 mg, 6.8 mmol) added and stirred 1 hour. 1-bromo-3-methyl butane (870 uL, 6.8 mmol) added and stirred overnight. Reaction was reduced in vacuo and taken up in DCM. This was washed with water, 1N NaOH then dried over magnesium sulfate filtered and reduced in vacuo to obtain 840 mg crude product to be used as is in next step. LRMS (ESI) m/z 245 [(M+H)]+, calc'd for $C_{10}H_{14}BrNO$: 244.13.

Part B.
(1-Isopentyl-2-oxo-1,2-dihydropyridin-4-yl)boronic acid

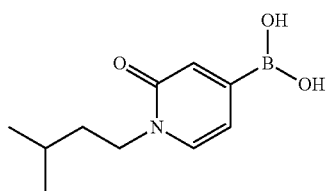

4-Bromo-1-isopentylpyridin-2(1H)-one (840 mg, 3.4 mmol) taken up in 10 mL dry DMF under nitrogen. Bis(pinacalato)diborane (1.3 g, 5.1 mmol), potassium acetate (1.01 g, 10.2 mmol), and $Pd(dppf)Cl_2$ dichloromethane (281 mg, 0.34 mmol) added, reaction heated to 85° C. and stirred overnight. Reaction cooled to room temperature and filtered through celite with DCM. This was reduced in vacuo taken up in 1N NaOH and washed with DCM. Aq layer then made acidic with 1N HCl and extracted with DCM. DCM layer dried over magnesium sulfate filtered and reduced in vacuo to yield 600 mg of crude for use in next step. LRMS (ESI) m/z 210 [(M+H)]+, calc'd for $C_{10}H_{16}BNO_3$: 209.05.

Part C. 1-Isopentyl-4-(pyrazolo[1,5-a]pyrimidin-5-yl)pyridin-2(1H)-one

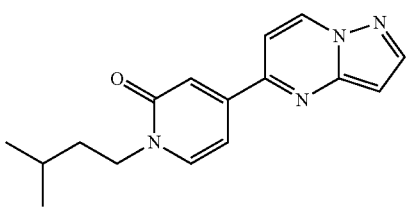 [SMILES: CC(C)CCn1ccc(-c2ccn3nccc3n2)cc1=O]

6-Chloro-imiadzo[1,2-b]pyridazine (400 mg, 2.6 mmol) taken up in 20 mL acetonitrile and 10 mL water. (1-isopentyl-2-oxo-1,2-dihydropyridin-4-yl)boronic acid (654 mg, 3.1 mmol), potassium carbonate (721 mg, 5.2 mmol), and $Pd(dppf)Cl_2$ dichloromethane (197 mg, 0.26 mmol) were added and the reaction mixture was stirred at 85° C. for 2 hours. Cooled to room temperature filtered through a celite plug with DCM and reduced in vacuo. Then, passed through a silica plug using DCM, dried in vacuo to get 646 mg crude product to carry on as is to next step. $^1$H NMR (400 MHz, DMSO-$d_6$) δ 9.19-9.26 (m, 1H), 8.30 (d, J=2.27 Hz, 1H), 7.85 (d, J=7.07 Hz, 1H), 7.67 (d, J=7.58 Hz, 1H), 7.20 (d, J=2.02 Hz, 1H), 7.01 (dd, J=2.02, 7.07 Hz, 1H), 6.85 (dd, J=0.63, 2.40 Hz, 1H), 3.91-3.99 (m, 2H), 1.48-1.65 (m, 3H), 0.94 (d, J=6.32 Hz, 6H) LRMS (ESI) m/z 283 [(M+H)]+, calc'd for $C_{16}H_{18}N_4O$: 282.35.

Part D. 4-(3-Bromopyrazolo[1,5-a]pyrimidin-5-yl)-1-isopentylpyridin-2(1H)-one

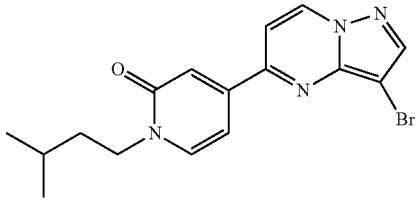 [SMILES: CC(C)CCn1ccc(-c2ccn3ncc(Br)c3n2)cc1=O]

1-Isopentyl-4-(pyrazolo[1,5-a]pyrimidin-5-yl)pyridin-2 (1H)-one (646 mg, 2.3 mmol) taken up in acetonitrile. N-bromo succinimide (400 mg, 2.3 mmol) added and reaction stirred for 4 hours. Reaction then stripped down in vacuo and taken up in ethyl acetate and washed with water, 1N NaOH, brine, and water. Organic layer dried over magnesium sulfate filtered and reduced in vacuo to obtain 653 mg crude product to be used in further reactions. $^1$H NMR (400 MHz, DMSO-$d_6$) d 9.28 (d, J=7.33 Hz, 1H), 8.46 (s, 1H), 7.88 (d, J=7.33 Hz, 1H), 7.77 (d, J=7.58 Hz, 1H), 7.25 (d, J=2.02 Hz, 1H), 7.03 (dd, J=1.89, 7.20 Hz, 1H), 3.93-3.99 (m, 2H), 1.53-1.63 (m, 3H), 0.94 (d, J=6.32 Hz, 6H). LRMS (ESI) m/z 361/363 [(M+H)]+, calc'd for $C_{16}H_{17}BrN_4O$: 361.24.

5.6.8. Synthesis of 1-Isopentyl-4-(3-(2-methoxypyridin-3-yl)pyrazolo[1,5-a]pyrimidin-5-yl)pyridin-2 (1H)-one

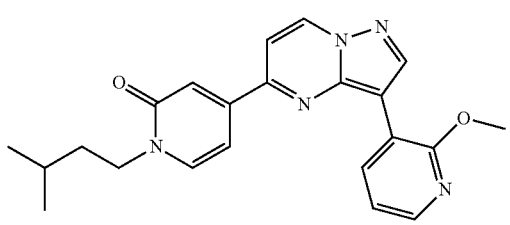 [SMILES: COc1ncccc1-c1cnn2ccc(-c3ccn(CCC(C)C)c(=O)c3)nc12]

4-(3-Bromopyrazolo[1,5-a]pyrimidin-5-yl)-1-isopentylpyridin-2(1H)-one (150 mg, 0.41 mmol), 2-methoxypyridine-3-boronic acid (127 mg, 0.82 mmol), potassium carbonate (172 mg, 1.23 mmol), Pd(OAc)$_2$ (2 mg, 0.0082 mmol), and x-Phos (8 mg, 0.0164 mmol) were taken up in 2 mL dioxane and 1 mL water in a sealed tube and heated at 85° C. for 2 hours. Reaction then cooled to room temperature filtered through a celite plug with acetonitrile and DCM, reduced in vacuo. Purified on Shimadzu neutral phase prep lyophilized to get 56 mg product. $^1$H NMR (400 MHz, DMSO-d6) d 9.31 (d, J=7.58 Hz, 1H), 8.88 (dd, J=1.77, 7.58 Hz, 1H), 8.83 (s, 1H), 8.13 (dd, J=1.77, 4.80 Hz, 1H), 7.89 (d, J=7.07 Hz, 1H), 7.78 (d, J=7.33 Hz, 1H), 7.27 (d, J=1.77 Hz, 1H), 7.20 (dd, J=4.80, 7.58 Hz, 1H), 7.07 (dd, J=2.02, 7.07 Hz, 1H), 4.04 (s, 3H), 3.97 (t, J=7.20 Hz, 2H), 1.58 (t, J=6.44 Hz, 3H), 0.95 (d, J=6.32 Hz, 6H). LRMS (ESI) m/z 390 [(M+H)]+, calc'd for $C_{22}H_{23}N_5O_2$: 389.46.

5.6.9. Synthesis of 5-(2-Isopropoxypyridin-4-yl)-3-(2-methoxypyridin-3-yl)pyrazolo[1,5-a]pyrimidine

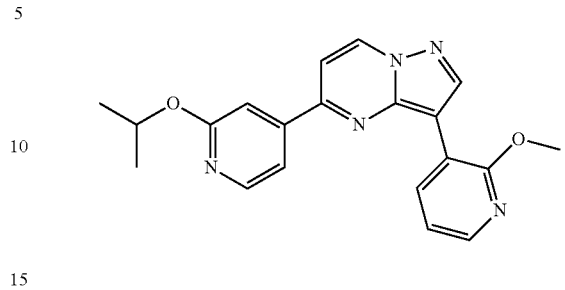

Part A. 5-(2-Isopropoxypyridin-4-yl)pyrazolo[1,5-a]pyrimidine

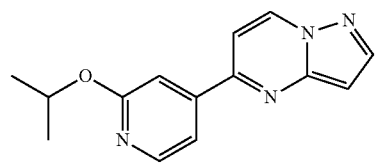 [SMILES: CC(C)Oc1cc(-c2ccn3nccc3n2)ccn1]

5-Chloropyrazolo[1,5-a]pyrimidine (500 mg, 3.25 mmol) taken up in 3 ml acetonitrile and 1.5 ml water. 2-isopropoxy-4-(4,4,5,5-tetramethyl-1,3,2-dioxaborolan-2-yl)pyridine (1 g, 3.9 mmol), Potassium carbonate (902 mg, 6.5 mmol), and Pd(dppf)Cl$_2$:DCM (267 mg, 0.325 mmol) added and reaction stirred in microwave in a sealed tube at 120° C. for 12 minutes. Reaction cooled filtered through celite washed through with ethyl acetate and reduced in vacuo. Reaction taken up in 1:1 ethyl acetate: hexane and filtered through a plug of celite. The filtrate was collected, dried in vacuo to obtain 740 mg of crude product to be used as is in next step. LRMS (ESI) m/z 255 [(M+H)]+, calc'd for $C_{14}H_{14}N_4O$: 254.2.

Part B. 3-Bromo-5-(2-isopropoxypyridin-4-yl)pyrazolo[1,5-a]pyrimidine

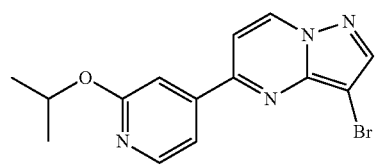 [SMILES: CC(C)Oc1cc(-c2ccn3ncc(Br)c3n2)ccn1]

5-(2-Isopropoxypyridin-4-yl)pyrazolo[1,5-a]pyrimidine (740 mg, 2.9 mmol) taken up in acetonitrile and N-bromo succinimide (570 mg, 3.19 mmol) added and stirred room temperature for 4 hours. Reaction stripped down in vacuo then taken up in ethyl acetate and washed with brine, 1N NaOH, and water, dried over magnesium sulfate filtered reduced in vacuo to obtain 970 mg crude product to use as is in next step. LRMS (ESI) m/z 334 [(M+H)]+, calc'd for $C_{14}H_{13}BrN_4O$: 333.2.

Part C. 5-(2-Isopropoxypyridin-4-yl)-3-(2-methoxy-pyridin-3-yl)pyrazolo[1,5-a]pyrimidine

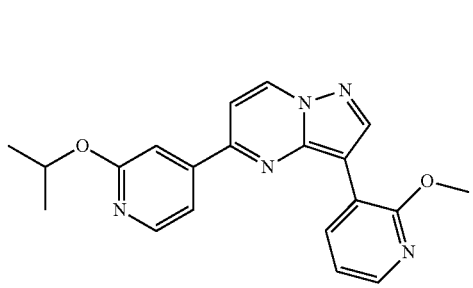 [SMILES: COc1ncccc1-c1cnn2ccc(-c3ccnc(OC(C)C)c3)nc12]

The titled compound was prepared using the Suzuki coupling procedure as described above in Example 5.6.8. ¹H NMR (400 MHz, DMSO-d₆) 9.34 (d, J=7.33 Hz, 1H), 8.91 (dd, J=1.89, 7.45 Hz, 1H), 8.83 (s, 1H), 8.34-8.41 (m, 1H), 8.13 (dd, J=1.89, 4.93 Hz, 1H), 7.85 (d, J=7.33 Hz, 1H), 7.80 (dd, J=1.52, 5.31 Hz, 1H), 7.56 (d, J=0.76 Hz, 1H), 7.23 (dd, J=4.93, 7.45 Hz, 1H), 5.35 (t, J=6.19 Hz, 1H), 4.04 (s, 3H), 1.36 (d, J=6.06 Hz, 6H). LRMS (ESI) m/z 362 [(M+H)]⁺, calc'd for $C_{20}H_{19}N_6O_2$: 361.4.

5.6.10. Synthesis of 3-(5-Fluoro-2-methoxyphenyl)-5-(2-methoxypyridin-4-yl)pyrazolo[1,5-a]pyrimidine

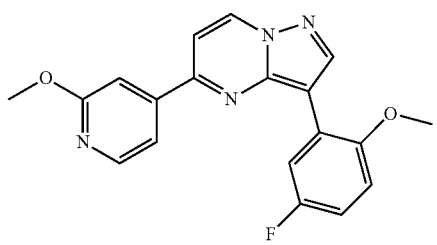

The titled compound was prepared as described in Example 5.6.9. ¹H NMR (400 MHz, DMSO-d₆) δ ppm 3.93 (s, 3H) 3.95 (s, 3H) 7.09-7.18 (m, 2H) 7.63 (s, 1H) 7.79-7.86 (m, 2H) 8.37-8.42 (m, 2H) 8.84 (s, 1H) 9.34 (d, J=7.33 Hz, 1H). LRMS (ESI) m/z 351.1 [(M+H)]⁺, calc'd for $C_{19}H_{16}FN_4O_2$: 350.35.

5.6.11. Synthesis of Isopropyl 4-(3-Bromopyrazolo[1,5-a]pyrimidin-5-yl)benzoate

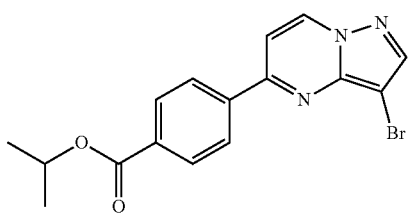 [SMILES: CC(C)OC(=O)c1ccc(-c2ccn3ncc(Br)c3n2)cc1]

Part A. Isopropyl 4-(pyrazolo[1,5-a]pyrimidin-5-yl)benzoate

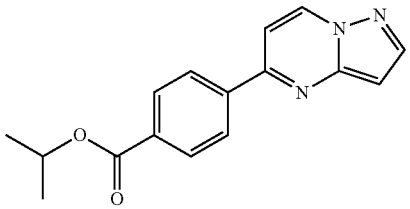 [SMILES: CC(C)OC(=O)c1ccc(-c2ccn3nccc3n2)cc1]

The Suzuki coupling procedure described as in Example 5.6.8 was carried out using triethylamine as base to obtain the desired product in 99% yield. ¹H NMR (400 MHz, CHLOROFORM-d) δ ppm 1.42 (d, J=6.32 Hz, 6H) 5.31 (dt, J=12.44, 6.28 Hz, 1H) 6.79 (d, J=2.02 Hz, 1H) 7.33 (d, J=7.33 Hz, 1H) 8.14-8.23 (m, 5H) 8.77 (dd, J=7.33, 0.51 Hz, 1H).

Part B. Isopropyl 4-(3-bromopyrazolo[1,5-a]pyrimidin-5-yl)benzoate

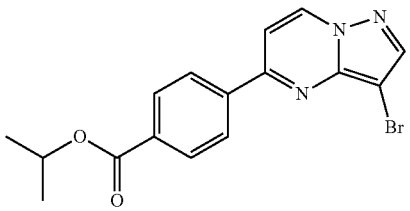 [SMILES: CC(C)OC(=O)c1ccc(-c2ccn3ncc(Br)c3n2)cc1]

The bromonation procedure described above in Example 5.6.6, part C, was used to obtain the titled compound. ¹H NMR (400 MHz, CHLOROFORM-d) δ ppm 1.43 (d, J=6.32 Hz, 7H) 5.32 (quin, J=6.25 Hz, 1H) 7.38 (d, J=7.33 Hz, 1H) 8.16-8.27 (m, 5H) 8.72 (d, J=7.33 Hz, 1H). LRMS (ESI) m/z 360 (M+H)⁺, (doublet at 362), calc'd for $C_{16}H_{14}BrN_3O_2$: 359.

5.6.12. Synthesis of Isopropyl 4-(3-iodopyrazolo[1,5-a]pyrimidin-5-yl)benzoate

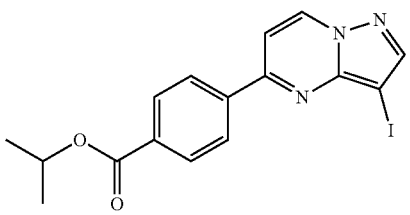 [SMILES: CC(C)OC(=O)c1ccc(-c2ccn3ncc(I)c3n2)cc1]

To 100 mg (0.356 mmol) of isopropyl 4-(imidazo[1,2-b]pyridazin-6-yl)benzoate dissolved in 3 mL DMF was added 88 mg (0.391 mmol) of NIS. The resulting mixture was stirred at room temperature overnight. It was diluted with EtOAc, washed twice with water and then brine, dried over MgSO₄, concentrated and purified on a 12 gram column on the ISCO eluting with 10-80% EtOAc/hexane to obtain 131 mg of the desired product (90% yield). ¹H NMR (400 MHz, CHLOROFORM-d) δ ppm 1.43 (d, J=6.32 Hz, 6H) 5.31 (quin, J=6.25 Hz, 1H) 7.38 (d, J=7.58 Hz, 1H) 8.15-8.33 (m, 5H) 8.73 (d, J=7.33 Hz, 1H). LRMS (ESI) m/z 408 [(M+H)]⁺, calc'd for $C_{16}H_{14}IN_3O_2$: 407.

5.6.13. Synthesis of 1-Isopentyl-4-(3-(2-methoxy-6-methylpyridin-3-yl)pyrazolo[1,5-a]pyrimidin-5-yl)pyridin-2(1H)-one

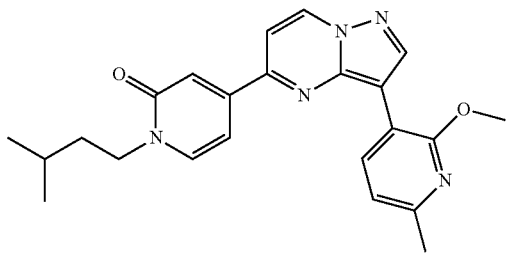 [SMILES: COc1nc(C)ccc1-c1cnn2ccc(-c3ccn(CCC(C)C)c(=O)c3)nc12]

The titled compound was prepared as described in Example 5.6.8. $^1$H NMR (400 MHz, DMSO-d$_6$) δ 9.28 (d, J=7.58 Hz, 1H), 8.78 (s, 1H), 8.73 (d, J=7.58 Hz, 1H), 7.88 (d, J=7.33 Hz, 1H), 7.75 (d, J=7.33 Hz, 1H), 7.25 (d, J=2.02 Hz, 1H), 6.99-7.08 (m, 2H), 4.02 (s, 3H), 3.97 (t, J=7.20 Hz, 2H), 2.46 (s, 3H), 1.58 (t, J=6.57 Hz, 3H), 0.94 (d, J=6.06 Hz, 6H) LRMS (ESI) m/z 404 [(M+H)]$^+$, calc'd for C$_{23}$H$_{25}$N$_5$O$_2$: 403.5.

5.6.14. Synthesis of 4-(3-(5-Fluoro-2-methoxypyridin-3-yl)pyrazolo[1,5-a]pyrimidin-5-yl)-1-isopentylpyridin-2(1H)-one

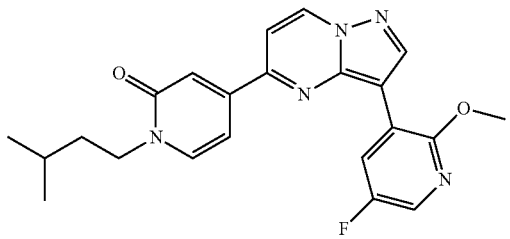 [SMILES: COc1ncc(F)cc1-c1cnn2ccc(-c3ccn(CCC(C)C)c(=O)c3)nc12]

The titled compound was prepared as described for in Example 5.6.8. $^1$H NMR (400 MHz, DMSO-d$_6$) δ 9.36 (d, J=7.33 Hz, 1H), 8.90 (s, 1H), 8.85 (dd, J=3.03, 10.11 Hz, 1H), 8.11 (d, J=2.78 Hz, 1H), 7.95 (d, J=7.07 Hz, 1H), 7.83 (d, J=7.33 Hz, 1H), 7.28 (d, J=1.77 Hz, 1H), 7.04 (dd, J=2.15, 7.20 Hz, 1H), 4.05 (s, 3H), 3.89-4.02 (m, 2H), 1.58 (t, J=6.06 Hz, 3H), 0.95 (d, J=6.06 Hz, 6H) LRMS (ESI) m/z 408 [(M+H)]$^+$, calc'd for C$_{22}$H$_{22}$FN$_5$O$_2$: 407.4.

5.6.15. Synthesis of 4-(3-(2-Ethoxypyridin-3-yl)pyrazolo[1,5-a]pyrimidin-5-yl)-1-isopentylpyridin-2(1H)-one

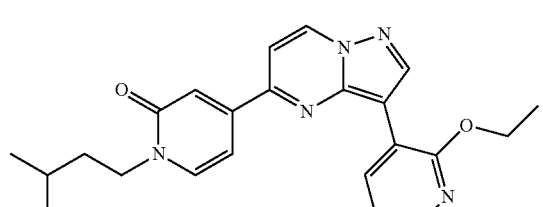

The titled compound was prepared as described in Example 5.6.8. $^1$H NMR (400 MHz, DMSO-d$_6$) δ 9.31 (d, J=7.58 Hz, 1H), 8.83-8.88 (m, 2H), 8.11 (dd, J=1.89, 4.93 Hz, 1H), 7.89 (d, J=7.07 Hz, 1H), 7.78 (d, J=7.33 Hz, 1H), 7.27 (d, J=2.02 Hz, 1H), 7.16-7.20 (m, 1H), 7.07 (dd, J=2.02, 7.07 Hz, 1H), 4.49 (q, J=7.07 Hz, 2H), 3.97 (t, J=7.20 Hz, 2H), 3.29 (br. s., 1H), 1.58 (t, J=6.32 Hz, 3H), 1.45 (t, J=7.07 Hz, 3H), 0.94 (d, J=6.06 Hz, 6H) LRMS (ESI) m/z 403 [(M+H)]$^+$, calc'd for C$_{23}$H$_{25}$N$_5$O$_2$: 403.49.

5.6.16. Synthesis of 4-(3-(5-Fluoro-2-methoxyphenyl)pyrazolo[1,5-a]pyrimidin-5-yl)-1-isopentylpyridin-2(1H)-one

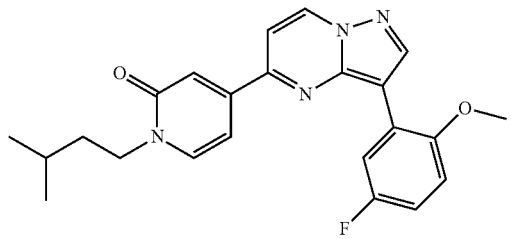 [SMILES: COc1ccc(F)cc1-c1cnn2ccc(-c3ccn(CCC(C)C)c(=O)c3)nc12]

The titled compound was prepared as described in Example 5.6.8. $^1$H NMR (400 MHz, DMSO-d$_6$) δ 9.25-9.35 (m, 1H), 8.84 (s, 1H), 8.31-8.42 (m, 1H), 7.89-7.98 (m, 1H), 7.72-7.81 (m, 1H), 7.23-7.31 (m, 1H), 7.08-7.21 (m, 2H), 6.94-7.06 (m, 1H), 3.94-4.01 (m, 2H), 3.93 (s, 3H), 1.48-1.63 (m, 3H), 0.94 (d, J=6.32 Hz, 6H) (ESI) m/z 407 [(M+H)]$^+$, calc'd for C$_{23}$H$_{23}$FN$_4$O$_2$: 406.4.

5.6.17. Synthesis of Isopropyl(4-(3-(2-methoxypyridin-3-yl)pyrazolo[1,5-a]pyrimidin-5-yl)butyl)(methyl)carbamate

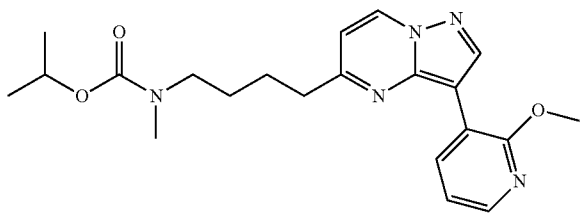 [SMILES: COc1ncccc1-c1cnn2ccc(CCCCN(C)C(=O)OC(C)C)nc12]

Part A. Isopropyl but-3-en-1-yl(methyl)carbamate

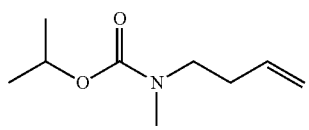

Starting with N-methylbut-3-en-1-amine, the procedure for the synthesis of isopropyl allyl(methyl)carbamate (in Example 5.6.6, part A) was followed to obtain the titled compound.

Part B. Isopropyl methyl(4-(pyrazolo[1,5-a]pyrimidin-5-yl)butyl)carbamate

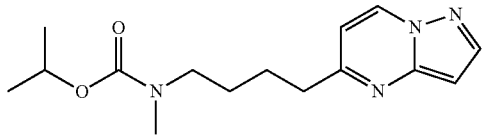 [SMILES: CC(C)OC(=O)N(C)CCCCc1ccn2nccc2n1]

The procedure described in Example 5.6.6, part B, was followed to obtain the titled compound. $^1$H NMR (400 MHz, CHLOROFORM-d) δ ppm 1.24 (d, J=5.81 Hz, 6H) 1.57-1.67 (m, 2H) 1.78-1.86 (m, 2H) 2.88 (t, J=7.58 Hz, 5H) 3.32 (br. s., 2H) 4.92 (dt, J=12.38, 6.19 Hz, 1H) 6.59 (d, J=1.52 Hz, 1H) 6.70 (d, J=7.07 Hz, 1H) 8.09 (d, J=2.27 Hz, 1H) 8.58 (d, J=7.07 Hz, 1H). LRMS (ESI) m/z 291 [(M+H)]$^+$, calc'd for $C_{15}H_{22}N_4O_2$: 290.

Part C. Isopropyl(4-(3-bromopyrazolo[1,5-a]pyrimidin-5-yl)butyl)(methyl)carbamate

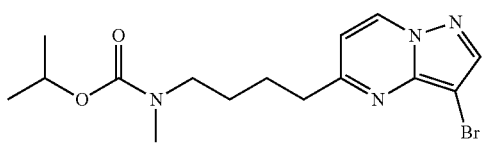 [SMILES: CC(C)OC(=O)N(C)CCCCc1ccn2ncc(Br)c2n1]

The bromonation procedure described in Example 5.6.6, part C, was followed to obtain the titled compound. $^1$H NMR (400 MHz, CHLOROFORM-d) δ ppm 1.25 (d, J=6.06 Hz, 6H) 1.63-1.68 (m, 2H) 1.77-1.85 (m, 2H) 2.92 (dd, J=15.66, 7.83 Hz, 5H) 3.33 (br. s., 2H) 4.92 (dt, J=12.19, 5.91 Hz, 1H) 6.70-6.82 (m, 1H) 8.07 (s, 1H) 8.52 (d, J=7.07 Hz, 1H). LRMS (ESI) m/z 369 [(M+H)]$^+$, (doublet at 371), calc'd for $C_{15}H_{21}BrN_4O_2$: 368.

Part D. Isopropyl(4-(3-(2-methoxypyridin-3-yl)pyrazolo[1,5-a]pyrimidin-5-yl)butyl)(methyl)carbamate

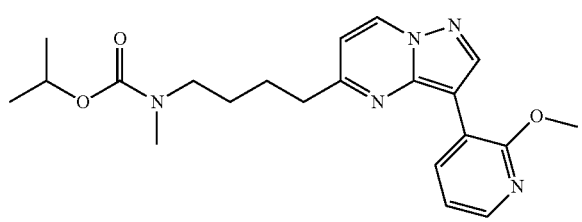 [SMILES: COc1ncccc1-c1cnn2ccc(CCCCN(C)C(=O)OC(C)C)nc12]

The Suzuki procedure described in Example 5.6.6, part D, was used to obtain the titled compound. $^1$H NMR (400 MHz, CHLOROFORM-d) δ ppm 1.20-1.30 (m, 6H) 1.63-1.74 (m, 2H) 1.81-1.91 (m, 2H) 2.84-2.99 (m, 5H) 3.35 (br. s., 2H) 4.12 (s, 3H) 4.92 (dt, J=12.44, 6.28 Hz, 1H) 6.75 (d, J=7.07 Hz, 1H) 7.05 (dd, J=7.58, 4.80 Hz, 1H) 8.10 (dd, J=4.93, 1.89 Hz, 1H) 8.60 (d, J=7.07 Hz, 1H) 8.79 (s, 1H) 8.89 (d, J=7.33 Hz, 1H). LRMS (ESI) m/z 398 [(M+H)]$^+$, calc'd for $C_{21}H_{27}N_5O_3$: 397.

5.6.18. Synthesis of 4-(3-Iodopyrazolo[1,5-a]pyrimidin-5-yl)-1-isopentylpyridin-2(1H)-one

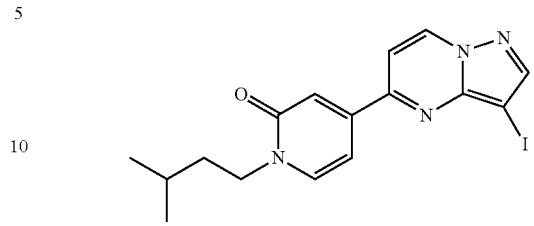

The iodation procedure described in Example 5.6.12 was followed to make the titled compound in 87% yield. $^1$H NMR (400 MHz, CHLOROFORM-d) δ ppm 1.02 (d, J=6.32 Hz, 6H) 1.66-1.74 (m, 3H) 4.00-4.07 (m, 2H) 7.14-7.21 (m, 2H) 7.26 (s, 1H) 7.43 (d, J=7.07 Hz, 1H) 8.21 (s, 1H) 8.73 (d, J=7.33 Hz, 1H). LRMS (ESI) m/z 409 [(M+H)]$^+$, calc'd for $C_{16}H_{17}IN_4O$: 408.

5.6.19. Synthesis of 1-Isopentyl-4-(3-(trifluoromethyl)pyrazolo[1,5-a]pyrimidin-5-yl)pyridin-2(1H)-one

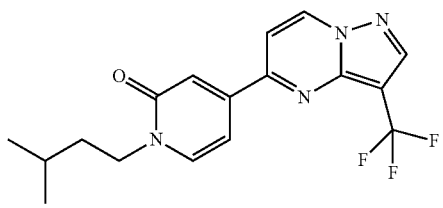 [SMILES: CC(C)CCn1ccc(-c2ccn3ncc(C(F)(F)F)c3n2)cc1=O]

To 123 mg (0.301 mmol) of 4-(3-iodopyrazolo[1,5-a]pyrimidin-5-yl)-1-isopentylpyridin-2(1H)-one dissolved in 5 mL of DMF was added 94 mg (0.301 mmol) of Trifluoromethyl(1,10-phenanthroline)copper, CAS#1300746-79-5. This mixture was heated to 40° C., and stirred for two days. It was then diluted with EtOAc, washed with brine, dried over MgSO$_4$, concentrated, and purified on the PREP HPLC to obtain the titled compound in 18% yield. $^1$H NMR (400 MHz, CHLOROFORM-d) δ ppm 1.02 (d, J=6.32 Hz, 6H) 1.65-1.75 (m, 3H) 4.00-4.07 (m, 2H) 7.14 (dd, J=7.07, 2.02 Hz, 1H) 7.20 (d, J=2.02 Hz, 1H) 7.44 (dd, J=7.20, 3.41 Hz, 2H) 8.38 (s, 1H) 8.82 (d, J=7.33 Hz, 1H). LRMS (ESI) m/z 351 [(M+H)]$^+$, calc'd for $C_{17}H_{17}F_3N_4O$: 350.

5.6.20. Synthesis of Isopropyl 4-(3-(2-methoxypyridin-3-yl)pyrazolo[1,5-a]pyrimidin-5-yl)benzoate

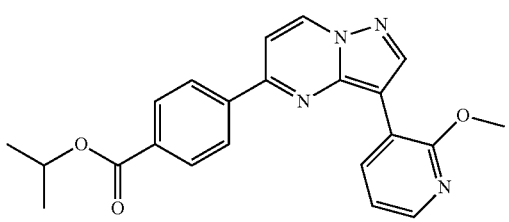 [SMILES: COc1ncccc1-c1cnn2ccc(-c3ccc(C(=O)OC(C)C)cc3)nc12]

The Suzuki procedure described in Example 5.6.6, part D, was followed to obtain the titled compound. $^1$H NMR (400

MHz, CHLOROFORM-d) δ ppm 1.41-1.46 (m, 6H) 4.14 (s, 3H) 5.26-5.39 (m, 1H) 7.10 (dd, J=7.45, 4.93 Hz, 1H) 7.38 (d, J=7.33 Hz, 1H) 8.14 (dd, J=4.80, 1.77 Hz, 1H) 8.20-8.26 (m, 4H) 8.78 (d, J=7.33 Hz, 1H) 8.87 (s, 1H) 8.99 (dd, J=7.45, 1.89 Hz, 1H). LRMS (ESI) m/z 389 [(M+H)]$^+$, calc'd for $C_{22}H_{20}N_4O_3$: 388.

5.6.21. Synthesis of 4-(3-Chloropyrazolo[1,5-a]pyrimidin-5-yl)-1-isopentylpyridin-2(1H)-one and 3-Chloro-4-(3-chloropyrazolo[1,5-a]pyrimidin-5-yl)-1-isopentylpyridin-2(1H)-one

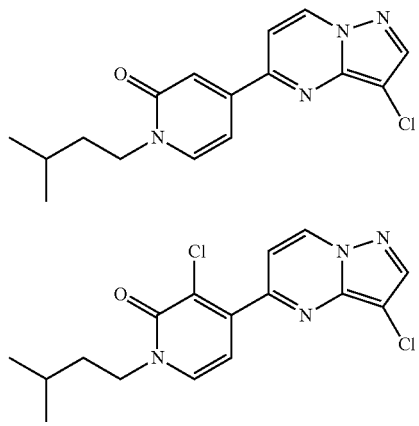

A

B 1-(3-Methyl-butyl)-4-pyrazolo[1,5-a]pyrimidin-5-yl-1H-pyridin-2-one (940 mg, 3.33 mmol) taken up in acetonitrile. N-chloro succinimide (445 mg, 6.6 mmol) added and reaction stirred at 40° C. overnight. The reaction mixture was then stripped down in vacuo and purified on Shimadzu neutral prep to obtain both products after lyopholization.

A, 19 mg obtained. $^1$H NMR (400 MHz, DMSO-d$_6$) δ 9.26 (d, J=7.58 Hz, 1H), 8.46 (s, 1H), 7.88 (d, J=7.33 Hz, 1H), 7.77 (d, J=7.58 Hz, 1H), 7.25 (d, J=1.77 Hz, 1H), 7.03 (dd, J=2.15, 7.20 Hz, 1H), 3.91-3.99 (m, 2H), 1.53-1.63 (m, 3H), 0.91-0.96 (m, 6H). LRMS (ESI) m/z 317 [(M+H)]$^+$, calc'd for $C_{16}H_{17}ClN_4O$: 316.7.

B, 112 mg obtained. $^1$H NMR (400 MHz, DMSO-d$_6$) δ 9.23-9.31 (m, 1H), 8.47-8.51 (m, 1H), 7.90 (d, J=7.07 Hz, 1H), 7.42 (d, J=7.33 Hz, 1H), 6.53 (d, J=6.82 Hz, 1H), 3.95-4.07 (m, 2H), 1.55-1.65 (m, 3H), 0.91-0.98 (m, 6H). LRMS (ESI) m/z 351 [(M+H)]$^+$, calc'd for $C_{16}H_{16}Cl_2N_4O$: 351.2.

5.6.22. Synthesis of 1-(3,3-Dimethylbutyl)-4-(3-(2-methoxypyridin-3-yl)pyrazolo[1,5-a]pyrimidin-5-yl)pyridin-2(1H)-one

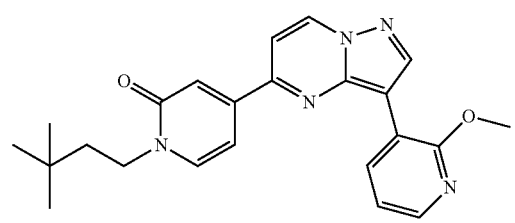 [SMILES: COc1ncccc1-c1cnn2ccc(-c3ccn(CCC(C)(C)C)c(=O)c3)nc12]

Part A.
4-Bromo-1-(3,3-dimethylbutyl)pyridin-2(1H)-one

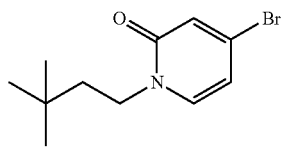

4-Bromo-2-hydroxy pyridine (600 mg, 3.4 mmol) was taken up in dry DMF under nitrogen. Sodium hydride 60% in oil (165 mg, 4.1 mmol) added and stirred 30 minutes. Lithium bromide (598 mg, 6.8 mmol) added and stirred 1 hour. 1-Bromo-3-methyl butane (870 uL, 6.8 mmol) was added and the resulting mixture was stirred for 3 days. The reaction mixture was reduced in vacuo and taken up in DCM. This was washed with water, 1N NaOH then dried over magnesium sulfate filtered and reduced in vacuo to obtain 860 mg crude product to be used as is in the next step. LRMS (ESI) m/z 258/260 [(M+H)]$^+$, calc'd for $C_{11}H_{16}BrNO$: 258.16.

Part B. (1-(3,3-Dimethylbutyl)-2-oxo-1,2-dihydropyridin-4-yl)boronic acid

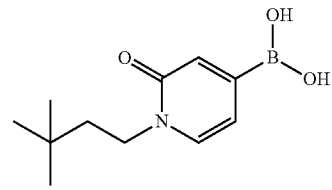 [SMILES: CC(C)(C)CCn1ccc(B(O)O)cc1=O]

4-Bromo-1-(3,3-dimethylbutyl)pyridin-2(1H)-one (860 mg, 3.3 mmol) taken up in 10 mL dry DMF under nitrogen. Bis(pinacalato)diborane (1.26 g, 5 mmol), potassium acetate (985 mg, 10 mmol), and Pd(dppf)Cl$_2$ dichloromethane (272 mg, 0.33 mmol) added, reaction heated to 85° C. and stirred overnight. Reaction cooled to room temperature and filtered through celite with DCM. This was reduced in vacuo taken up in 1N NaOH and washed with DCM. The aqueous layer was then made acidic with 1N HCl and extracted with DCM. DCM layer dried over magnesium sulfate filtered and reduced in vacuo to yield 740 mg of crude to use in further reaction. LRMS (ESI) m/z 224 [(M+H)]$^+$, calc'd for $C_{11}H_{18}BNO_3$: 223.08.

Part C. 1-(3,3-Dimethylbutyl)-4-(pyrazolo[1,5-a]pyrimidin-5-yl)pyridin-2(1H)-one

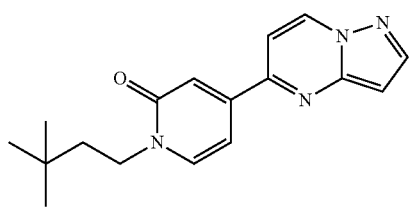 [SMILES: CC(C)(C)CCn1ccc(-c2ccn3nccc3n2)cc1=O]

6-Chloro-imiadzo[1,2-b]pyridazine (420 mg, 2.74 mmol) taken up in 20 mL acetonitrile and 10 mL water. (1-(3,3-dimethylbutyl)-2-oxo-1,2-dihydropyridin-4-yl)boronic acid (740 mg, 3.3 mmol), potassium carbonate (755 mg, 5.48 mmol), and Pd(dppf)Cl$_2$ dichloromethane (224 mg, 0.274 mmol) added and reaction stirred at 85° C. for 2 hrs. Cooled to room temperature filtered through a celite plug with DCM and reduced in vacuo. The residue was passed through a silica plug using DCM, dried in vacuo, to get 438 mg of crude product to carry on as is to next step. LRMS (ESI) m/z 297 [(M+H)]$^+$, calc'd for C$_{17}$H$_2$ON$_4$O: 296.38.

Part D. 4-(3-Bromopyrazolo[1,5-a]pyrimidin-5-yl)-1-(3,3-dimethylbutyl)pyridin-2(1H)-one

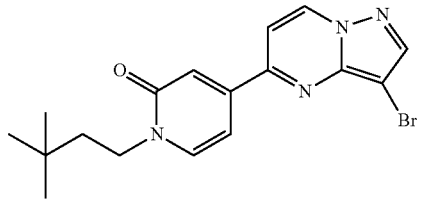

1-(3,3-Dimethylbutyl)-4-(pyrazolo[1,5-a]pyrimidin-5-yl)pyridin-2(1H)-one (438 mg, 1.48 mmol) taken up in acetonitrile. N-bromo succinimide (263 mg, 1.48 mmol) added and reaction stirred for 4 hours. The reaction mixture was then stripped down in vacuo and taken up in ethyl acetate and washed with water, 1N NaOH, brine, and water. Organic layer dried over magnesium sulfate filtered and reduced in vacuo to obtain 522 mg crude product to be used in further reactions. LRMS (ESI) m/z 375/377 [(M+H)]$^+$, calc'd for C$_{17}$H$_{19}$BrN$_4$O: 375.27.

Part E. 1-(3,3-Dimethylbutyl)-4-(3-(2-methoxypyridin-3-yl)pyrazolo[1,5-a]pyrimidin-5-yl)pyridin-2(1H)-one

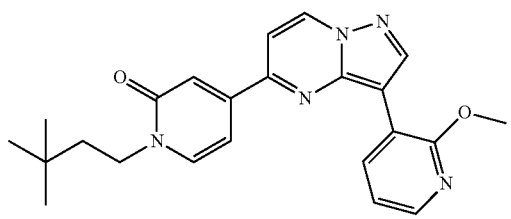 [SMILES: COc1ncccc1-c1cnn2ccc(-c3ccn(CCC(C)(C)C)c(=O)c3)nc12]

4-(3-Bromo-pyrazolo[1,5-a]pyrimidin-5-yl)-1-(3-methylbutyl)-1H-pyridin-2-one (150 mg, 0.4 mmol), 2-methoxypyridine-3-boronic acid (122 mg, 0.8 mmol), potassium carbonate (165 mg, 1.2 mmol), Pd(OAc)$_2$ (2 mg, 0.08 mmol), and x-Phos (8 mg, 0.16 mmol) were taken up in 2 mL dioxane and 1 mL water in a sealed tube and heated at 85° C. for 2 hours. Reaction then cooled to room temperature filtered through a celite plug with acetonitrile and DCM, reduced in vacuo. Purified on Shimadzu neutral phase prep lyophilized to get 26 mg product. $^1$H NMR (400 MHz, DMSO-d6) δ 9.31 (d, J=7.33 Hz, 1H), 8.83 (s, 2H), 8.11-8.15 (m, 1H), 7.91 (d, J=7.07 Hz, 1H), 7.78 (d, J=7.33 Hz, 1H), 7.25 (d, J=2.02 Hz, 1H), 7.16-7.22 (m, 1H), 7.04-7.09 (m, 1H), 4.04 (s, 5H), 1.50-1.60 (m, 2H), 0.98 (s, 9H). LRMS (ESI) m/z 404 [(M+H)]$^+$, calc'd for C$_{23}$H$_{25}$N$_5$O$_2$: 403.49.

5.6.23. Synthesis of 4-(3-(2-Methoxypyridin-3-yl)pyrazolo[1,5-a]pyrimidin-5-yl)-1-(3,3,3-trifluoropropyl)pyridin-2(1H)-one

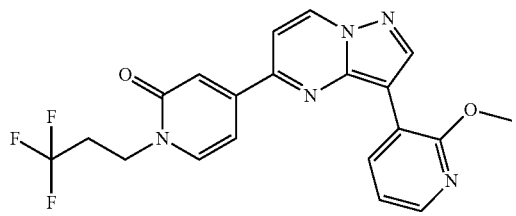 [SMILES: COc1ncccc1-c1cnn2ccc(-c3ccn(CCC(F)(F)F)c(=O)c3)nc12]

Part A. 4-Bromo-1-(3,3,3-trifluoropropyl)pyridin-2(1H)-one

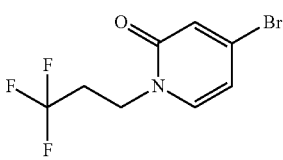 [SMILES: O=c1cc(Br)ccn1CCC(F)(F)F]

4-Bromo-2-hydroxy pyridine (400 mg, 2.3 mmol), 1-Iodo-3,3,3-trifluoropropane (3 g, 13.8 mmol), and potassium carbonate (3.17 g, 23 mmol) taken up in THF in a sealed tube and stirred at 80° C. overnight. Reaction reduced in vacuo, and purified on ISCO silica column with hexane and ethyl acetate 5-100%. Product fractions reduced in vacuo to obtain 445 mg product. LRMS (ESI) m/z 270/272 [(M+H)]$^+$, calc'd for C$_8$H$_7$BrF$_3$NO: 270.05.

Part B. (2-Oxo-1-(3,3,3-trifluoropropyl)-1,2-dihydropyridin-4-yl)boronic acid

4-Bromo-1-(3,3,3-trifluoropropyl)pyridin-2(1H)-one (445 mg, 1.65 mmol) taken up in dioxane under nitrogen. Bis(pinacalato)diborane (627 mg, 2.48 mmol), potassium acetate (242 mg, 2.48 mmol), Pd$_2$(dba)$_3$ (10 mg, 0.0165 mmol), and triphenylphosphine (9 mg, 0.033 mmol) were added and the reaction mixture was heated to 85° C. and stirred for 4 hours. The reaction mixture was cooled to room temperature and filtered through celite with DCM. This was reduced in vacuo to yield 500 mg of crude, for use in further reaction. LRMS (ESI) m/z 235 [(M+H)]$^+$, calc'd for C$_8$H$_9$BF$_3$NO$_3$: 234.97.

Part C. 4-(Pyrazolo[1,5-a]pyrimidin-5-yl)-1-(3,3,3-trifluoropropyl)pyridin-2(1H)-one

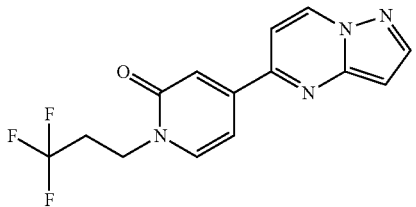 [SMILES: O=c1cc(-c2ccn3nccc3n2)ccn1CCC(F)(F)F]

6-Chloro-imiadzo[1,2-b]pyridazine (243 mg, 0.766 mmol) taken up in 20 mL acetonitrile and 10 mL water. (2-oxo-1-(3,3,3-trifluoropropyl)-1,2-dihydropyridin-4-yl) boronic acid (500 mg, 0.766 mmol), potassium carbonate (653 mg, 2.3 mmol), and Pd(dppf)Cl$_2$ dichloromethane (13 mg, 0.0.00766 mmol) added and reaction stirred at 85° C. for 2 hrs. Cooled to room temperature filtered through a celite plug with DCM and reduced in vacuo to get 260 mg crude product to carry on as is to next step. LRMS (ESI) m/z 309 [(M+H)]$^+$, calc'd for C$_{14}$H$_{11}$F$_3$N$_4$O: 308.27.

Part D. 4-(3-Bromopyrazolo[1,5-a]pyrimidin-5-yl)-1-(3,3,3-trifluoropropyl)pyridin-2(1H)-one

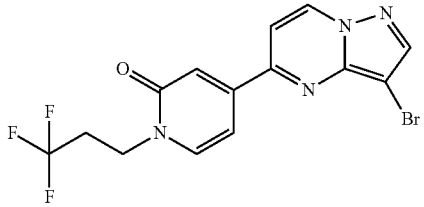 [SMILES: O=c1cc(-c2ccn3ncc(Br)c3n2)ccn1CCC(F)(F)F]

4-(Pyrazolo[1,5-a]pyrimidin-5-yl)-1-(3,3,3-trifluoropropyl)pyridin-2(1H)-one (260 mg, 0.84 mmol) taken up in acetonitrile. N-bromo succinimide (151 mg, 0.84 mmol) added and reaction stirred for 4 hours. Reaction then stripped down in vacuo and taken up in ethyl acetate and washed with water, 1N NaOH, brine, and water. Organic layer dried over magnesium sulfate filtered and reduced in vacuo purified on Isco silica column with hexane: ethyl acetate 5-100%, product fractions reduced in vacuo to get 70 mg product to be used in further reactions. LRMS (ESI) m/z 387/389 [(M+H)]$^+$, calc'd for C$_{14}$H$_{10}$BrF$_3$N$_4$O: 387.1.

Part E. 4-(3-(2-Methoxypyridin-3-yl)pyrazolo[1,5-a]pyrimidin-5-yl)-1-(3,3,3-trifluoropropyl)pyridin-2(1H)-one

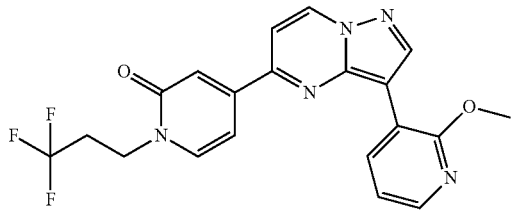 [SMILES: COc1ncccc1-c1cnn2ccc(-c3ccn(CCC(F)(F)F)c(=O)c3)nc12]

4-(3-Bromopyrazolo[1,5-a]pyrimidin-5-yl)-1-(3,3,3-trifluoropropyl)pyridin-2(1H)-one (70 mg, 0.18 mmol), 2-methoxypyridine-3-boronic acid (55 mg, 0.36 mmol), triethylamine (151 uL, 1.08 mmol), and Pd132 (4 mg, 0.0054 mmol) were taken up in 4 mL dioxane and 1 mL water in a sealed tube and heated at 85° C. for 2 hours. Reaction then cooled to room temperature filtered through a celite plug with acetonitrile and DCM, reduced in vacuo. Product recrystallized from acetonitrile and dried to get 47 mg product $^1$H NMR (400 MHz, DMSO-d6) δ d 9.34 (d, J=7.33 Hz, 1H), 8.88 (dd, J=1.89, 7.45 Hz, 1H), 8.84 (s, 1H), 8.13 (dd, J=1.89, 4.93 Hz, 1H), 7.93 (d, J=7.07 Hz, 1H), 7.81 (d, J=7.33 Hz, 1H), 7.33 (d, J=1.77 Hz, 1H), 7.21 (dd, J=4.80, 7.58 Hz, 1H), 7.12 (dd, J=2.02, 7.07 Hz, 1H), 4.22 (t, J=6.82 Hz, 2H), 4.04 (s, 3H), 2.80 (d, J=11.37 Hz, 2H) LRMS (ESI) m/z 416 [(M+H)]$^+$, calc'd for C$_{20}$H$_{16}$F$_3$N$_6$O$_2$: 415.3.

5.6.24. Synthesis of 1-Isobutyl-4-(3-(2-methoxypyridin-3-yl)pyrazolo[1,5-a]pyrimidin-5-yl)pyridin-2(1H)-one

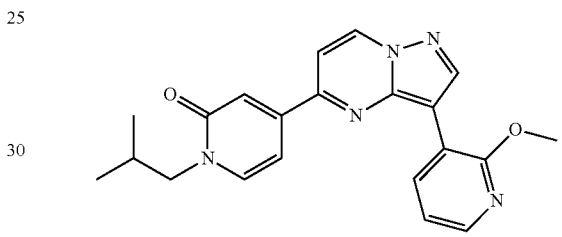

The procedure described in Example 5.6.23 was used to obtain the titled compound. $^1$H NMR (DMSO-d$_6$) δ: 9.33 (d, J=7.3 Hz, 1H), 8.90 (dd, J=7.5, 1.9 Hz, 1H), 8.84 (s, 1H), 8.13 (dd, J=4.9, 1.9 Hz, 1H), 7.85 (d, J=7.1 Hz, 1H), 7.80 (d, J=7.3 Hz, 1H), 7.30 (d, J=1.8 Hz, 1H), 7.21 (dd, J=7.5, 4.9 Hz, 1H), 7.08 (dd, J=7.2, 2.1 Hz, 1H), 4.04 (s, 3H), 3.79 (d, J=7.3 Hz, 2H), 1.98-2.19 (m, 1H), 0.86-0.94 (m, 6H) LRMS (ESI) m/z 376 [(M+H)]$^+$, calc'd for C$_{21}$H$_{21}$N$_6$O$_2$: 375.43.

5.6.25. Synthesis of 1-(3,3-Dimethylbutyl)-4-(3-(5-fluoro-2-methoxypyridin-3-yl)pyrazolo[1,5-a]pyrimidin-5-yl)pyridin-2(1H)-one

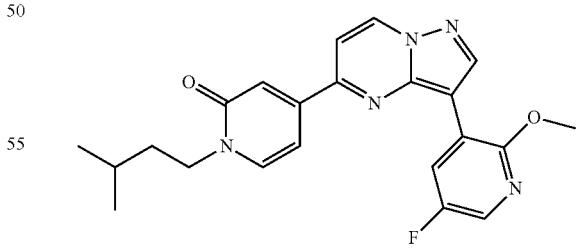

The procedure described in Example 5.6.23 was used to obtain the titled compound. $^1$H NMR (DMSO-d$_6$) δ: 9.37 (d, J=7.3 Hz, 1H), 8.91 (s, 1H), 8.81-8.89 (m, 1H), 8.12 (d, J=3.0 Hz, 1H), 7.99 (d, J=7.3 Hz, 1H), 7.85 (d, J=7.3 Hz, 1H), 7.29 (d, J=1.8 Hz, 1H), 6.96-7.10 (m, 1H), 4.06 (s, 3H), 3.87-4.02 (m, 2H), 1.51-1.64 (m, 2H), 0.99 (s, 9H) LRMS (ESI) m/z 422 [(M+H)]$^+$, calc'd for C$_{23}$H$_{24}$FN$_5$O$_2$: 421.48.

5.6.26. Synthesis of 1-(2-Methoxyethyl)-4-(3-(2-methoxypyridin-3-yl)pyrazolo[1,5-a]pyrimidin-5-yl)pyridin-2(1H)-one

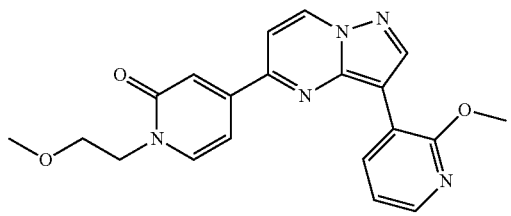

The procedure for described in Example 5.6.23 was used to obtain the titled compound. $^1$H NMR (DMSO-d$_6$) δ: 9.31 (d, J=7.6 Hz, 1H), 8.89 (dd, J=7.6, 1.8 Hz, 1H), 8.84 (s, 1H), 8.13 (dd, J=4.8, 1.8 Hz, 1H), 7.79 (dd, J=13.0, 7.2 Hz, 2H), 7.28 (d, J=1.8 Hz, 1H), 7.21 (dd, J=7.5, 4.9 Hz, 1H), 7.06 (dd, J=7.2, 1.9 Hz, 1H), 4.14 (t, J=5.3 Hz, 2H), 4.04 (s, 3H), 3.63 (t, J=5.3 Hz, 2H), 3.27 (s, 3H) LRMS (ESI) m/z 378 [(M+H)]$^+$, calc'd for C$_{20}$H$_{19}$N$_5$O$_3$: 377.41.

5.6.27. Synthesis of 4-(3-(5-Fluoro-2-methoxyphenyl)pyrazolo[1,5-a]pyrimidin-5-yl)-1-isobutylpyridin-2(1H)-one

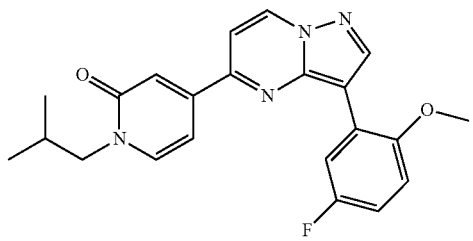 [SMILES: COc1ccc(F)cc1-c1cnn2ccc(-c3ccn(CC(C)C)c(=O)c3)nc12]

The procedure described in Example 5.6.23 was used to obtain the titled compound. $^1$H NMR (DMSO-d$_6$) δ: 9.30 (d, J=7.3 Hz, 1H), 8.83 (s, 1H), 8.36 (dd, J=10.6, 3.0 Hz, 1H), 7.88 (d, J=7.3 Hz, 1H), 7.78 (d, J=7.3 Hz, 1H), 7.28 (d, J=1.8 Hz, 1H), 7.07-7.20 (m, 2H), 7.02 (dd, J=7.2, 1.9 Hz, 1H), 3.93 (s, 3H), 3.78 (d, J=7.6 Hz, 2H), 2.13 (s, 1H), 0.90 (d, J=6.8 Hz, 6H). LRMS (ESI) m/z 393 [(M+H)]$^+$, calc'd for C$_{22}$H$_{21}$FN$_4$O$_2$: 392.44.

Synthesis of 1-(3,3-Dimethylbutyl)-4-(3-(5-fluoro-2-methoxyphenyl)pyrazolo[1,5-a]pyrimidin-5-yl)pyridin-2(1H)-one

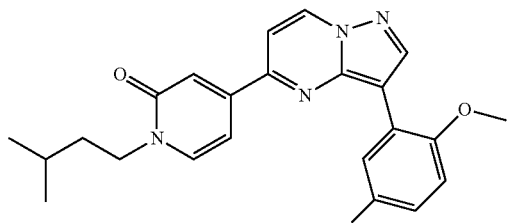

The procedure described in Example 5.6.23 was used to obtain the titled compound. $^1$H NMR (DMSO-d$_6$) δ: 9.29 (d, J=7.3 Hz, 1H), 8.84 (s, 1H), 8.32-8.41 (m, 1H), 7.92-7.99 (m, 1H), 7.74-7.81 (m, 1H), 7.25 (d, J=1.8 Hz, 1H), 7.08-7.20 (m, 2H), 6.98-7.06 (m, 1H), 3.93 (s, 5H), 1.47-1.64 (m, 2H), 0.98 (s, 9H) LRMS (ESI) m/z 421 [(M+H)]$^+$, calc'd for C$_{24}$H$_{25}$FN$_4$O$_2$: 420.49.

5.6.28. Synthesis of 1-(3,3-Dimethylbutyl)-4-(3-(2-methoxy-6-methylpyridin-3-yl)pyrazolo[1,5-a]pyrimidin-5-yl)pyridin-2(1H)-one

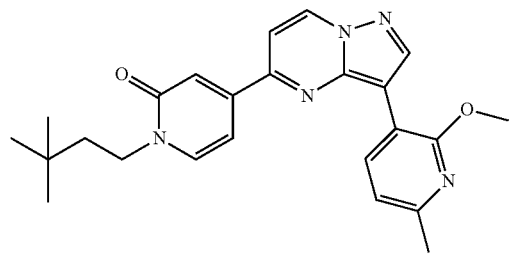 [SMILES: COc1nc(C)ccc1-c1cnn2ccc(-c3ccn(CCC(C)(C)C)c(=O)c3)nc12]

The procedure described in Example 5.6.23 was used to obtain the titled compound. $^1$H NMR (DMSO-d$_6$) δ: 9.28 (d, J=7.6 Hz, 1H), 8.78 (s, 1H), 8.73 (d, J=7.6 Hz, 1H), 7.90 (d, J=7.1 Hz, 1H), 7.75 (d, J=7.3 Hz, 1H), 7.24 (d, J=1.8 Hz, 1H), 7.00-7.07 (m, 2H), 4.02 (s, 3H), 3.92-4.00 (m, 2H), 2.46 (s, 3H), 1.50-1.61 (m, 2H), 0.98 (s, 9H) LRMS (ESI) m/z 418 [(M+H)]$^+$, calc'd for C$_{24}$H$_{27}$N$_5$O$_2$: 417.52.

5.6.29. Synthesis of 1-(2-Isopropoxyethyl)-4-(3-(2-methoxypyridin-3-yl)pyrazolo[1,5-a]pyrimidin-5-yl)pyridin-2(1H)-one

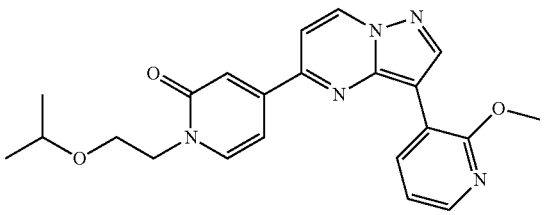 [SMILES: COc1ncccc1-c1cnn2ccc(-c3ccn(CCOC(C)C)c(=O)c3)nc12]

The procedure described in Example 5.6.23 was used to obtain the titled compound. $^1$H NMR (DMSO-d$_6$) δ: 9.32 (d, J=7.3 Hz, 1H), 8.89 (dd, J=7.5, 1.9 Hz, 1H), 8.84 (s, 1H), 8.13 (dd, J=4.9, 1.9 Hz, 1H), 7.80 (t, J=6.9 Hz, 2H), 7.29 (d, J=1.8 Hz, 1H), 7.21 (dd, J=7.6, 4.8 Hz, 1H), 7.07 (dd, J=7.1, 2.0 Hz, 1H), 4.09 (t, J=5.4 Hz, 2H), 4.04 (s, 3H), 3.65 (t, J=5.4 Hz, 2H), 3.49-3.60 (m, 1H), 1.05 (d, J=6.1 Hz, 6H) LRMS (ESI) m/z 406 [(M+H)]$^+$, calc'd for C$_{22}$H$_{23}$N$_5$O$_3$: 405.46.

5.6.30. Synthesis of 4-(3-(5-Fluoro-2-methoxypyridin-3-yl)pyrazolo[1,5-a]pyrimidin-5-yl)-1-(3,3,3-trifluoropropyl)pyridin-2(1H)-one

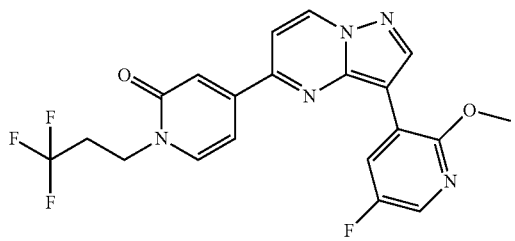 [SMILES: COc1ncc(F)cc1-c1cnn2ccc(-c3ccn(CCC(F)(F)F)c(=O)c3)nc12]

The procedure described in Example 5.6.23 was used to obtain the titled compound. ¹H NMR (400 MHz, DMSO-d₆) δ 9.35 (d, J=7.33 Hz, 1H), 8.87 (s, 1H), 8.81 (dd, J=3.03, 9.85 Hz, 1H), 8.08 (d, J=3.03 Hz, 1H), 7.97 (d, J=7.07 Hz, 1H), 7.82 (d, J=7.33 Hz, 1H), 7.31 (d, J=1.77 Hz, 1H), 7.05 (dd, J=1.89, 7.20 Hz, 1H), 4.21 (t, J=6.95 Hz, 2H), 4.04 (s, 3H), 2.72-2.90 (m, 2H) LRMS (ESI) m/z 434 [(M+H)]⁺, calc'd for $C_{20}H_{15}F_4N_5O_2$: 433.37.

5.6.31. Synthesis of 4-(3-(5-Fluoro-2-methoxyphenyl)pyrazolo[1,5-a]pyrimidin-5-yl)-1-(3,3,3-trifluoropropyl)pyridin-2(1H)-one

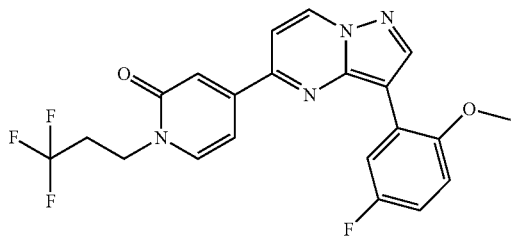 [SMILES: COc1ccc(F)cc1-c1cnn2ccc(-c3ccn(CCC(F)(F)F)c(=O)c3)nc12]

The procedure described in Example 5.6.23 was used to obtain the titled compound. ¹H NMR (400 MHz, DMSO-d₆) δ 9.32 (d, J=7.58 Hz, 1H), 8.84 (s, 1H), 8.36 (dd, J=3.03, 10.61 Hz, 1H), 7.97 (d, J=7.07 Hz, 1H), 7.80 (d, J=7.33 Hz, 1H), 7.32 (s, 1H), 7.09-7.23 (m, 2H), 7.06 (dd, J=1.77, 7.07 Hz, 1H), 4.21 (t, J=6.95 Hz, 2H), 3.93 (s, 3H), 2.71-2.89 (m, 2H) LRMS (ESI) m/z 4433 [(M+H)]⁺, calc'd for $C_{21}H_{16}F_4N_4O_2$: 432.

5.6.32. Synthesis of 4-(3-(2-Methoxy-6-methylpyridin-3-yl)pyrazolo[1,5-a]pyrimidin-5-yl)-1-(3,3,3-trifluoropropyl)pyridin-2(1H)-one

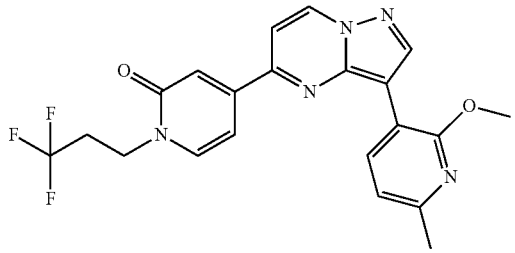 [SMILES: COc1nc(C)ccc1-c1cnn2ccc(-c3ccn(CCC(F)(F)F)c(=O)c3)nc12]

The procedure described in Example 5.6.23 was used to obtain the titled compound. ¹H NMR (DMSO-d₆) δ: 9.28 (d, J=7.3 Hz, 1H), 8.77 (s, 1H), 8.72 (d, J=7.6 Hz, 1H), 7.91 (d, J=7.3 Hz, 1H), 7.75 (d, J=7.6 Hz, 1H), 7.29 (d, J=1.8 Hz, 1H), 7.08 (dd, J=7.1, 2.0 Hz, 1H), 7.03 (d, J=7.6 Hz, 1H), 4.21 (t, J=6.9 Hz, 2H), 4.01 (s, 3H), 2.72-2.88 (m, 2H), 2.45 (s, 3H) LRMS (ESI) m/z 430 [(M+H)]⁺, calc'd for $C_{21}H_{18}F_3N_5O_2$: 429.3.

5.6.33. Synthesis of 4-(3-(2-Methoxypyridin-3-yl)pyrazolo[1,5-a]pyrimidin-5-yl)-1-(2-morpholinoethyl)pyridin-2(1H)-one

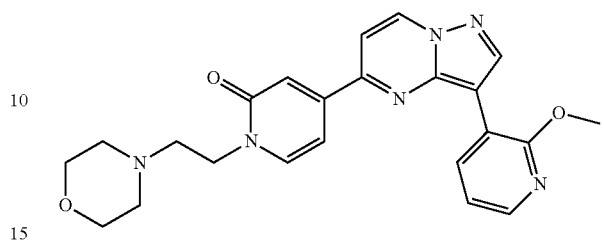

The procedure described in Example 5.6.23 was used to obtain the titled compound. ¹H NMR (400 MHz, DMSO-d₆) δ 9.31 (d, J=7.28 Hz, 1H), 8.88 (dd, J=1.76, 7.53 Hz, 1H), 8.83 (s, 1H), 8.13 (dd, J=1.88, 4.89 Hz, 1H), 7.86 (d, J=7.28 Hz, 1H), 7.78 (d, J=7.53 Hz, 1H), 7.27 (d, J=2.01 Hz, 1H), 7.21 (dd, J=4.77, 7.53 Hz, 1H), 7.07 (dd, J=2.13, 7.15 Hz, 1H), 4.07 (t, J=6.27 Hz, 2H), 4.04 (s, 3H), 3.49-3.61 (m, 4H), 2.61 (t, J=6.40 Hz, 2H), 2.46 (d, J=4.27 Hz, 4H) LRMS (ESI) m/z 433 [(M+H)]⁺, calc'd for $C_{23}H_{24}N_6O_3$: 432.49.

5.6.34. P81 Filter Plate Assay

Compounds were serially diluted into a Labcyte LDV plate (Labcyte, cat# LP-0200) using a Mutiprobe (PerkinElmer) and Biomek FX (Beckman Coulter) so that the highest compound concentration was at 96 μM. Compounds were then pinged (75 nL per well) into a Greiner 384-well reaction plate (Greiner, #781076) using an ECHO 550 Liquid Handler (Labcyte). A total of 12 μl reaction buffer (IMAP buffer containing Tween and DTT, from Molecular Devices) was then added to each well of columns 1 and 13 for the negative controls and 12 μl of 2×AAK1 (0.2 nM full-length human protein, NCBI accession no. NP_055726.2) was added to the remaining wells. Enzyme was then pre-incubated with compound for 10 minutes at RT. Reactions were initiated upon Minitrak (PerkinElmer) addition of 12 μl substrate mix containing 2×Mu2 (0.2 μM, full length human protein), 2× cold ATP (2 μM), and 1.3 μCi of hot ³³P-ATP. Reactions proceeded for one hour at RT. Meanwhile, Millipore 384-well P81 filter plates (Millipore, catalog # MZPHN0W10) were placed on a plate washer (Zoom ZW, from Titertek) and pre-wet with 50 μl % phosphoric acid. Kinase reactions were then stopped upon addition of 24 μl of 2% phosphoric acid to each well and the Minitrak was then used to transfer 40 μl from each well into the pre-wet Millipore 384-well P81 filter plates. Reaction mixtures were incubated for 10 minutes at room temperature in the P81 plates, followed by washing five times with 100 μl/well of 1% phosphoric acid using the Zoom filter washer. The bottom of each filter plate was sealed followed by addition of 20 μl Microscint 40 to each well, sealing the top of the plates with Flashplate cover, and then waiting one hour until reading on the TopCount (PerkinElmer).

5.6.35. HEK281 Cell-Based Assay

HEK293F cells were cultured in media containing DMEM (Gibco, cat. #11965), 10% FBS (SAFC Biosciences, cat. #12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat.#11668-019). The DNA was comprised of a mixture (per 10 cm dish) containing 3 ug AAK1/HA/pIRES (full length human, NCBI accession no. NP_055726.2), 45 μg Flag/AP2MI/pcDNA (full length human), and 1.5 ml OPTI-MEM. The Lipofectamine 2000 is made up of a mixture (per 10 cm dish) containing 144 μl Lipofectamine 2000 and 1.5 ml OPTI-MEM. Each mixture was transferred to individual 15 ml tubes and incubated at room temperature for 5 minutes, and then the two mixes were combined and incubated at room temperature for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% $CO_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 μl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 μl of cell suspension transferred into each well of 96-well TC plate. Finally, 100 μl of 2× compound diluted in DMEM+0.5% FBS was then added into wells containing cell suspension for a 1× final concentration. Plates were then incubated at 37° C. and 5% $CO_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1×LDS-PAGE sample buffer (Invitrogen, cat.# NP0008)+2× Halt phophatase and protease inhibitor cocktail (Thermo Scientific, cat.#1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 μl per sample was loaded into each lane of a 4-20% Tris-Glycine Criterion 26-well gel (Biorad, cat.#345-0034) for the phospho-mu2 blot and 10 μl per lane in a 4-12% Bis-Tris (+MES buffer) NuPAGE 26-well gel (Invitrogen, cat.# WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500; Sigma, cat.# F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; BioRad, cat.#170-6515) or anti-mouse-HRP (1:2000; Biorad, cat.#170-6516) in TBST+5% milk for 1 hour at RT, washed 3× for 10 minutes with TBST, and developed with ECL reagent (GE Healthcare, cat.# RPN2132) on a Versadoc. Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. $IC_{50}$ values were then calculated using Excel fitting software.

5.6.36. In Vitro Data

In vitro data obtained for various compounds of the invention are provided below in Table 1, wherein "MW" means molecular weight, "P81 Assay" refers to the P81 filter plate assay described above, "CBA" refers to the HEK281 cell-based assay described above, "-" means that results for the given assay were not obtained, "*" means less than or equal to 1.0 μM, "" means a value of less than or equal to 0.1 μM, and "*" means less than or equal to 0.01 μM.

TABLE 1

| Compound | MW | CBA $IC_{50}$ μM | P81 $IC_{50}$ μM |
|---|---|---|---|
| tert-butyl 4-(pyrazolo[1,5-a]pyrimidin-5-yl)-5,6-dihydropyridine-1(2H)-carboxylate | 300.4 | ** | — |
| 5-(1,2,3,6-tetrahydropyridin-4-yl)pyrazolo[1,5-a]pyrimidine | 200.2 | >0.3 | — |
| isopropyl 4-(3-(2-methoxypyridin-3-yl)pyrazolo[1,5-a]pyrimidin-5-yl)-5,6-dihydropyridine-1(2H)-carboxylate | 393.4 | *** | *** |
| isopropyl 4-(3-(2-methoxypyridin-3-yl)pyrazolo[1,5-a]pyrimidin-5-yl)piperidine-1-carboxylate | 395.5 | *** | >0.3 |
| 3-(5-fluoro-2-methoxyphenyl)-5-(2-methoxypyridin-4-yl)pyrazolo[1,5-a]pyrimidine | 350.3 | *** | * |
| (5-(2-isopropoxypyridin-4-yl)pyrazolo[1,5-a]pyrimidin-3-yl)methanol | 284.3 | >0.3 | — |
| isopropyl methyl(3-(pyrazolo[1,5-a]pyrimidin-5-yl)propyl)carbamate | 276.3 | >0.3 | >0.1 |
| isopropyl (3-(3-(2-methoxypyridin-3-yl)pyrazolo[1,5-a]pyrimidin-5-yl)propyl)(methyl)carbamate | 383.4 | ** | — |
| 5-(2-isopropoxypyridin-4-yl)-3-(2-methoxypyridin-3-yl)pyrazolo[1,5-a]pyrimidine | 361.4 | *** | ** |
| 1-isopentyl-4-(3-(2-methoxypyridin-3-yl)pyrazolo[1,5-a]pyrimidin-5-yl)pyridin-2(1H)-one | 389.5 | *** | *** |
| 4-(3-bromopyrazolo[1,5-a]pyrimidin-5-yl)-1-isopentylpyridin-2(1H)-one | 361.2 | *** | *** |
| 1-isopentyl-4-(pyrazolo[1,5-a]pyrimidin-5-yl)pyridin-2(1H)-one | 282.3 | ** | — |

TABLE 1-continued

| Compound | MW | CBA IC$_{50}$ μM | P81 IC$_{50}$ μM |
|---|---|---|---|
| isopropyl 4-(pyrazolo[1,5-a]pyrimidin-5-yl)benzoate | 281.3 | * | — |
| isopropyl 4-(3-bromopyrazolo[1,5-a]pyrimidin-5-yl)benzoate | 360.2 | ** | — |
| isopropyl 4-(3-iodopyrazolo[1,5-a]pyrimidin-5-yl)benzoate | 407.2 | ** | — |
| 1-isopentyl-4-(3-(2-methoxy-6-methylpyridin-3-yl)pyrazolo[1,5-a]pyrimidin-5-yl)pyridin-2(1H)-one | 403.5 | *** | *** |
| 4-(3-(5-fluoro-2-methoxypyridin-3-yl)pyrazolo[1,5-a]pyrimidin-5-yl)-1-isopentylpyridin-2(1H)-one | 407.4 | *** | *** |
| 4-(3-(2-ethoxypyridin-3-yl)pyrazolo[1,5-a]pyrimidin-5-yl)-1-isopentylpyridin-2(1H)-one | 403.5 | *** | *** |
| 4-(3-(5-fluoro-2-methoxyphenyl)pyrazolo[1,5-a]pyrimidin-5-yl)-1-isopentylpyridin-2(1H)-one | 406.5 | *** | *** |
| isopropyl (4-(3-bromopyrazolo[1,5-a]pyrimidin-5-yl)butyl)(methyl)carbamate | 369.3 | >0.3 | — |
| isopropyl (4-(3-(2-methoxypyridin-3-yl)pyrazolo[1,5-a]pyrimidin-5-yl)butyl)(methyl)carbamate | 397.5 | ** | — |
| 4-(3-iodopyrazolo[1,5-a]pyrimidin-5-yl)-1-isopentylpyridin-2(1H)-one | 408.2 | *** | *** |
| 1-isopentyl-4-(3-(trifluoromethyl)pyrazolo[1,5-a]pyrimidin-5-yl)pyridin-2(1H)-one | 350.3 | ** | — |
| isopropyl 4-(3-(2-methoxypyridin-3-yl)pyrazolo[1,5-a]pyrimidin-5-yl)benzoate | 388.4 | *** | — |
| 4-(3-chloropyrazolo[1,5-a]pyrimidin-5-yl)-1-isopentylpyridin-2(1H)-one | 316.8 | *** | ** |
| 3-chloro-4-(3-chloropyrazolo[1,5-a]pyrimidin-5-yl)-1-isopentylpyridin-2(1H)-one | 351.2 | ** | — |
| 4-(3-bromopyrazolo[1,5-a]pyrimidin-5-yl)-1-(3,3-dimethylbutyl)pyridin-2(1H)-one | 375.3 | ** | — |
| 1-(3,3-dimethylbutyl)-4-(3-(2-methoxypyridin-3-yl)pyrazolo[1,5-a]pyrimidin-5-yl)pyridin-2(1H)-one | 403.5 | *** | *** |
| 4-(3-(2-methoxypyridin-3-yl)pyrazolo[1,5-a]pyrimidin-5-yl)-1-(3,3,3-trifluoropropyl)pyridin-2(1H)-one | 415.4 | *** | *** |
| 1-isobutyl-4-(3-(2-methoxypyridin-3-yl)pyrazolo[1,5-a]pyrimidin-5-yl)pyridin-2(1H)-one | 375.4 | *** | *** |
| 1-(3,3-dimethylbutyl)-4-(3-(5-fluoro-2-methoxypyridin-3-yl)pyrazolo[1,5-a]pyrimidin-5-yl)pyridin-2(1H)-one | 421.5 | *** | *** |
| 1-(2-methoxyethyl)-4-(3-(2-methoxypyridin-3-yl)pyrazolo[1,5-a]pyrimidin-5-yl)pyridin-2(1H)-one | 377.4 | *** | *** |
| 4-(3-(5-fluoro-2-methoxyphenyl)pyrazolo[1,5-a]pyrimidin-5-yl)-1-isobutylpyridin-2(1H)-one | 392.4 | *** | *** |
| 1-(3,3-dimethylbutyl)-4-(3-(5-fluoro-2-methoxyphenyl)pyrazolo[1,5-a]pyrimidin-5-yl)pyridin-2(1H)-one | 420.5 | *** | *** |
| 1-(3,3-dimethylbutyl)-4-(3-(2-methoxy-6-methylpyridin-3-yl)pyrazolo[1,5-a]pyrimidin-5-yl)pyridin-2(1H)-one | 417.5 | — | — |
| 1-(2-isopropoxyethyl)-4-(3-(2-methoxypyridin-3-yl)pyrazolo[1,5-a]pyrimidin-5-yl)pyridin-2(1H)-one | 405.4 | *** | ** |
| 4-(3-(5-fluoro-2-methoxypyridin-3-yl)pyrazolo[1,5-a]pyrimidin-5-yl)-1-(3,3,3-trifluoropropyl)pyridin-2(1H)-one | 433.4 | *** | *** |
| 4-(3-(5-fluoro-2-methoxyphenyl)pyrazolo[1,5-a]pyrimidin-5-yl)-1-(3,3,3-trifluoropropyl)pyridin-2(1H)-one | 432.4 | *** | ** |
| 4-(3-(2-methoxy-6-methylpyridin-3-yl)pyrazolo[1,5-a]pyrimidin-5-yl)-1-(3,3,3-trifluoropropyl)pyridin-2(1H)-one | 429.4 | *** | ** |
| 4-(3-(2-methoxypyridin-3-yl)pyrazolo[1,5-a]pyrimidin-5-yl)-1-(2-morpholinoethyl)pyridin-2(1H)-one | 432.5 | *** | *** |

All publications (e.g., patents and patent applications) cited above are incorporated herein by reference in their entireties.

What is claimed is:

1. A compound of the formula:

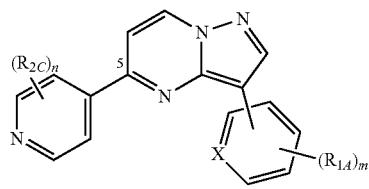

or a pharmaceutically acceptable salt thereof, wherein:
X is CH or N;
each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more RIB;
each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo;
each $R_{1C}$ is independently hydrogen or optionally substituted $C_{1-12}$ hydrocarbyl or 2-12-membered heterocarbyl, which optional substitution is with one or more of cyano, halo or hydroxyl;

each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, oxo, or optionally substituted $C_{1-22}$ hydrocarbyl or 2-12-membered heterocarbyl, which optional substitution is with one or more amino, cyano, halo, hydroxyl, or $R_{2D}$;

each $R_{2D}$ is independently hydrogen or optionally substituted $C_{1-12}$ hydrocarbyl or 2-12-membered heterocarbyl, which optional substitution is with one or more of amino, cyano, halo, hydroxyl;

n is 1-3; and m is 0-3.

2. The compound of claim 1, which is of the formula:

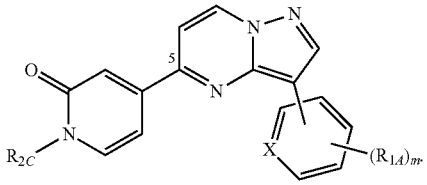

3. The compound of claim 1, wherein X is N and m is 1 or 2.

4. The compound of claim 2, which is of the formula:

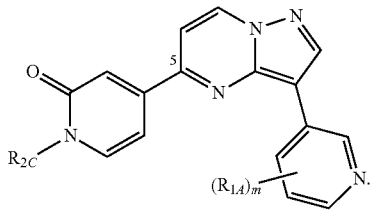

5. The compound of claim 4, which is of the formula:

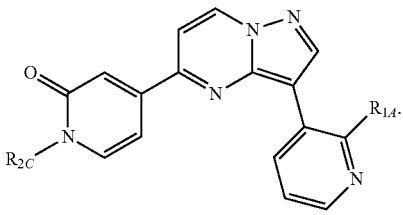

6. The compound of claim 4, which is of the formula:

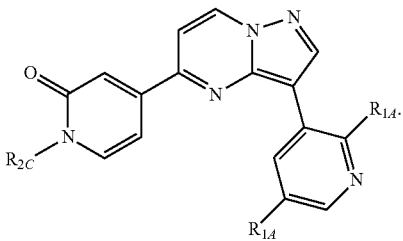

7. The compound of claim 1, wherein at least one $R_{1A}$ is halo.

8. The compound of claim 1, wherein at least one $R_{1A}$ is —$OR_{1C}$.

9. The compound of claim 8, wherein $R_{1C}$ is optionally substituted $C_{1-12}$ hydrocarbyl.

10. The compound of claim 1, wherein $R_{2C}$ is optionally substituted $C_{1-6}$ hydrocarbyl.

11. The compound of claim 1, wherein each $R_{2D}$ is independently hydrogen or $C_{1-12}$ hydrocarbyl.

12. The compound of claim 1, wherein at least one $R_{2D}$ is optionally substituted $C_{1-12}$ hydrocarbyl, which optional substitution is with one or more of amino, cyano, halo, hydroxyl.

13. The compound of claim 1, wherein $R_{2D}$ is 2-12-membered heterocarbyl comprising at least one nitrogen atom.

* * * * *